(12) United States Patent
Kamon

(10) Patent No.: US 11,398,033 B2
(45) Date of Patent: Jul. 26, 2022

(54) DIAGNOSIS SUPPORT SYSTEM, ENDOSCOPE SYSTEM, PROCESSOR, AND DIAGNOSIS SUPPORT METHOD

(71) Applicant: FUJIFILM Corporation, Tokyo (JP)

(72) Inventor: Shumpei Kamon, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 217 days.

(21) Appl. No.: 16/795,522

(22) Filed: Feb. 19, 2020

(65) Prior Publication Data

US 2020/0193602 A1    Jun. 18, 2020

Related U.S. Application Data

(63) Continuation of application No. PCT/JP2018/025873, filed on Jul. 9, 2018.

(30) Foreign Application Priority Data

Sep. 7, 2017 (JP) .............................. JP2017-172325

(51) Int. Cl.
*G06T 7/00* (2017.01)
*G06T 7/11* (2017.01)
(Continued)

(52) U.S. Cl.
CPC ........ *G06T 7/0016* (2013.01); *A61B 1/00045* (2013.01); *A61B 1/0051* (2013.01);
(Continued)

(58) Field of Classification Search
CPC .......... A61B 1/00006; A61B 1/000094; A61B 1/000096; A61B 1/00045; A61B 1/0051;
(Continued)

(56) References Cited

U.S. PATENT DOCUMENTS 10,154,778 B2    12/2018   Ojima et al.
2006/0015004 A1   1/2006   Sitzmann
(Continued)

FOREIGN PATENT DOCUMENTS

CN    101043843    9/2007
EP    1780651      5/2007
(Continued)

OTHER PUBLICATIONS

Machine translation of JP 2016-158752 (Year: 2016).*
(Continued)

*Primary Examiner* — Katrina R Fujita
(74) *Attorney, Agent, or Firm* — JCIPRNET

(57) ABSTRACT

A diagnosis support system having a processor configured to acquire medical images; detect a medicine and/or equipment used when the medical images are captured, from the medical images by image recognition; detect a region of interest from the medical images by image recognition; assign, to the medical image from which the medicine and/or equipment is detected, first detection information indicating the detected medicine and/or equipment; and assign, to the medical image from which the region of interest is detected, second detection information indicating the detected region of interest, display, on a display device, the medical images in a list in a display form according to the first detection information and the second detection information.

12 Claims, 19 Drawing Sheets

(51) Int. Cl.
  *A61B 1/00* (2006.01)
  *A61B 1/005* (2006.01)
(52) U.S. Cl.
  CPC ...... *G06T 7/11* (2017.01); *G06T 2207/10016* (2013.01); *G06T 2207/10068* (2013.01); *G06T 2207/30096* (2013.01)
(58) Field of Classification Search
  CPC ......... A61B 1/045; G06T 7/0016; G06T 7/11; G06T 2207/10016; G06T 2207/10068; G06T 2207/30096; G16H 30/40; G16H 40/63; G16H 50/20
  See application file for complete search history.

(56) References Cited

U.S. PATENT DOCUMENTS

| | | | | |
|---|---|---|---|---|
| 2010/0182412 | A1* | 7/2010 | Taniguchi | G16H 10/60 345/473 |
| 2013/0152020 | A1 | 6/2013 | Nishiyama | |
| 2015/0161802 | A1* | 6/2015 | Christiansen | A61B 90/94 348/74 |
| 2016/0048637 | A1* | 2/2016 | Nishiyama | G06F 16/54 382/305 |
| 2019/0053857 | A1* | 2/2019 | Sugie | A61B 1/00 |
| 2020/0082529 | A1* | 3/2020 | Mikami | H04N 13/239 |

FOREIGN PATENT DOCUMENTS

| | | |
|---|---|---|
| EP | 3031386 | 6/2016 |
| JP | 2016007444 | 1/2016 |
| JP | 2016062488 | 4/2016 |
| JP | 2016067782 | 5/2016 |
| JP | 5985084 | 9/2016 |
| JP | 2016158752 | 9/2016 |
| JP | 2017086685 | 5/2017 |
| WO | 2009008125 | 1/2009 |
| WO | 2010017531 | 2/2010 |
| WO | 2012132840 | 10/2012 |
| WO | 2015194580 | 12/2015 |

OTHER PUBLICATIONS

Machine translation of JP 2016-067782 (Year: 2016).*
"International Search Report (Form PCT/ISA/210) of PCT/JP2018/025873," dated Sep. 11, 2018, with English translation thereof, pp. 1-4.
"Written Opinion of the International Searching Authority (Form PCT/ISA/237) of PCT/JP2018/025873," dated Sep. 11, 2018, with English translation thereof, pp. 1-12.
"Office Action of Japan Counterpart Application" with English translation thereof, dated Aug. 10, 2021, p. 1-p. 9.
"Office Action of Japan Counterpart Application" with English translation thereof, dated Mar. 8, 2021, p. 1-p. 5.
"Search Report of Europe Counterpart Application", dated Sep. 15, 2020, p. 1-p. 9.
"Office Action of China Counterpart Application", dated Dec. 3, 2021, with English translation thereof, p. 1-p. 21.

* cited by examiner

| IMAGE ID | TYPE | FIRST DETECTION INFORMATION | SECOND DETECTION INFORMATION |
|---|---|---|---|
| i101 | CAPTURED IMAGE | MEDICINE: NOT DETECTED | REGION OF INTEREST: NOT DETECTED |
| i201 | DESIGNATED IMAGE | MEDICINE: DETECTED (INDIGO CARMINE) | REGION OF INTEREST: TUMORE DETECTED (3 mm) |
| ⋮ | ⋮ | ⋮ | ⋮ |
| i901 | DESIGNATED IMAGE | EQUIPMENT: DETECTED (BIOPSY FORCEPS) | REGION OF INTEREST: TUMORE DETECTED (5 mm) |
| ⋮ | ⋮ | ⋮ | ⋮ |

FIG. 10

| C07 | V07 | A07 |
|---|---|---|
| DISPLAY FORM OF MEDICINE | CHARACTER DIAPLAY | ▼ |
| C08 | V08 | A08 |
| DISPLAY FORM OF EQUIPMENT | PROCEDURE NAME | ▼ |
| C09 | V09 | A09 |
| DISTINGUISHABLE DISPLAY FORM OF IMAGE WITH REGION OF INTEREST DETECTED | ADD FRAME | ▼ |
| C10 | V10 | A10 |
| DISPLAY ONLY IMAGE WITH REGION OF INTEREST DETECTED | OFF | ▼ |
| C11 | V11 | A11 |
| DISPLAY IMAGE FOR EACH TYPE OF MEDICINE | ON | ▼ |
| C12 | V12 | A12 |
| DISPLAY ONLY IMAGE FOR SPECIFIC TYPE OF MEDICINE | ON | ▼ |

B01    B02    B03

[ OK ]    [ CANCEL ]    [ INITIAL SETTING ]

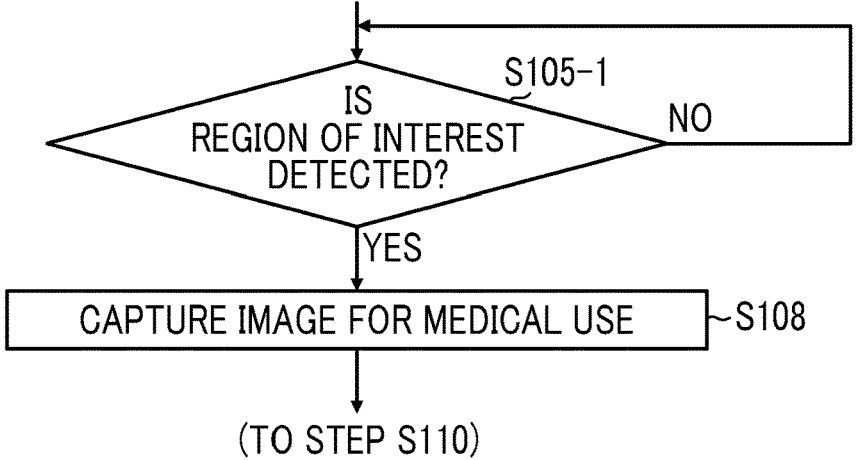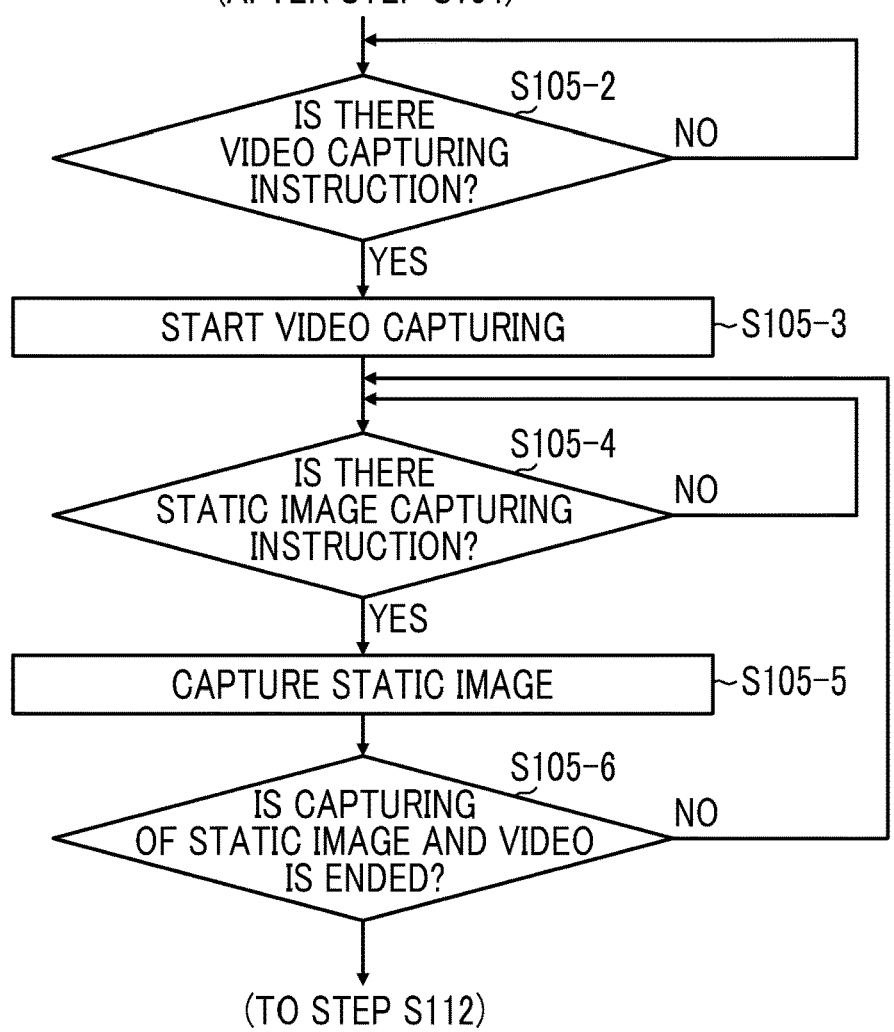

DIAGNOSIS SUPPORT SYSTEM, ENDOSCOPE SYSTEM, PROCESSOR, AND DIAGNOSIS SUPPORT METHOD

CROSS-REFERENCE TO RELATED APPLICATIONS

This application is a Continuation of PCT International Application No. PCT/JP2018/025873 filed on Jul. 9, 2018, which claims priority under 35 U.S.C § 119(a) to Japanese Patent Application No. 2017-172325 filed on Sep. 7, 2017. Each of the above application(s) is hereby expressly incorporated by reference, in its entirety, into the present application.

BACKGROUND OF THE INVENTION

1. Field of the Invention

The present invention relates to a diagnosis support system, an endoscope system, a processor, and a diagnosis support method.

2. Description of the Related Art

In diagnosis using medical equipment, an image of an object to be examined may be acquired by performing inspection or treatment using a medicine and/or equipment in some cases. In this case, the medicine and/or equipment used, contents of a procedure, and the like are necessary to be described in a report created after the diagnosis. However, the work load of a user such as a doctor is large, and thus a technique for reducing the work load is known.

For example, JP2016-062488A discloses that the medicine and/or equipment used in the inspection is detected from an endoscopic image by image recognition, resulting in assistance to perform an input operation for creating a medical document (endoscopy report, inspection record) by a health professional on the basis of the detection result. Specifically, in the endoscopy report, detection information or reflection information extracted from the detection information is automatically input to a treatment information field in a treatment area, and a procedure field, an addition field, a medicine filed, and an equipment field in a carrying-out field. Further, JP2016-062488A discloses that the name of the detected medicine and/or equipment is displayed (the medicine name and the treatment tool name are displayed in the tag of the image).

SUMMARY OF THE INVENTION

In a case of performing inspection based on the image acquired by an endoscope or the like, a relationship between the medicine and/or equipment used and a region of interest (lesion, lesion candidate, or the like) (what kind of medicine and/or equipment is used for which region of interest) is important. However, such a relationship is not considered in JP2016-062488A, and thus it is difficult to grasp the relationship between the medicine and/or equipment and the region of interest. It is burdensome for the user to relate the medicine and/or equipment and the region of interest, and there is a risk of error.

In this manner, in the related technique, the usefulness of the presented information is low, and it is difficult for a user to efficiently perform diagnosis, report creation, and the like based on the image.

The invention has been made in consideration of the above-described circumstances, and an object of the invention is to provide a diagnosis support system, an endoscope system, a processor, and a diagnosis support method which can present useful information to a user.

In order to achieve the above-described object, a diagnosis support system including a processor configured to: acquire a plurality of medical images; detect a medicine and/or equipment from the plurality of medical images by image recognition; detect a region of interest from the plurality of medical images by image recognition; assign, to the medical image from which the medicine and/or equipment is detected, first detection information indicating the detected medicine and/or equipment; and assign, to the medical image from which the region of interest is detected, second detection information indicating the detected region of interest, display, on a display device, the plurality of medical images in a list in a display form according to the first detection information and the second detection information.

According to the first aspect, since the first detection information indicating the detected medicine and/or equipment and the second detection information indicating the detected region of interest are assigned to an image for medical use, and images are displayed in a list in an aspect according to the detection information, it is possible for a user to easily grasp a relationship between the medicine and/or equipment, the region of interest, and the image. In this manner, according to the first aspect, it is possible to present useful information to a user, and it is possible for a user to efficiently perform diagnosis, report creation, and the like.

In the first aspect and the respective aspects to be described below, the "medicine" includes a pigment and a dye for observing the shape, unevenness, and the like of the region of interest (lesion area or the like), and the "equipment (instrument)" includes a treatment tool for performing biopsies, excision, and the like on an object to be examined. Further, the "region of interest" includes a lesion region, a lesion candidate region, a region after the treatment. In the first aspect, the image-for-medical-use acquisition unit may acquire a plurality of images for medical use by capturing images by the image pick-up device including the imaging optical system and the image pick-up element.

In the first aspect and the respective aspects to be described below, the image for medical use is referred to as a medical image. As a light source used for capturing an image for medical use, a light source that generates light in a white-light wavelength range or light in a plurality of wavelength ranges (narrow-band light) as the white-light wavelength range, infrared light, and excitation light can be used. Further, the image for medical use acquired in the first aspect may be a normal light image obtained from the application of light in a white-light wavelength range or light in a plurality of wavelength ranges as the light in a white-light wavelength range, or may be a special light image including information about the specific wavelength range on the basis of the normal light image.

BRIEF DESCRIPTION OF THE DRAWINGS

FIG. 10 is a diagram showing an example of a display condition setting screen.

FIG. 18 is a flowchart showing processing of automatic imaging according to detection of a region of interest.

FIG. 19 is a flowchart showing an aspect of capturing a static image while capturing a video.

DESCRIPTION OF THE PREFERRED EMBODIMENTS

A diagnosis support system, an endoscope system, a processor, and a diagnosis support method according to embodiments of the invention will be described in detail below with reference to the accompanying drawings.

First Embodiment

Figure 1:
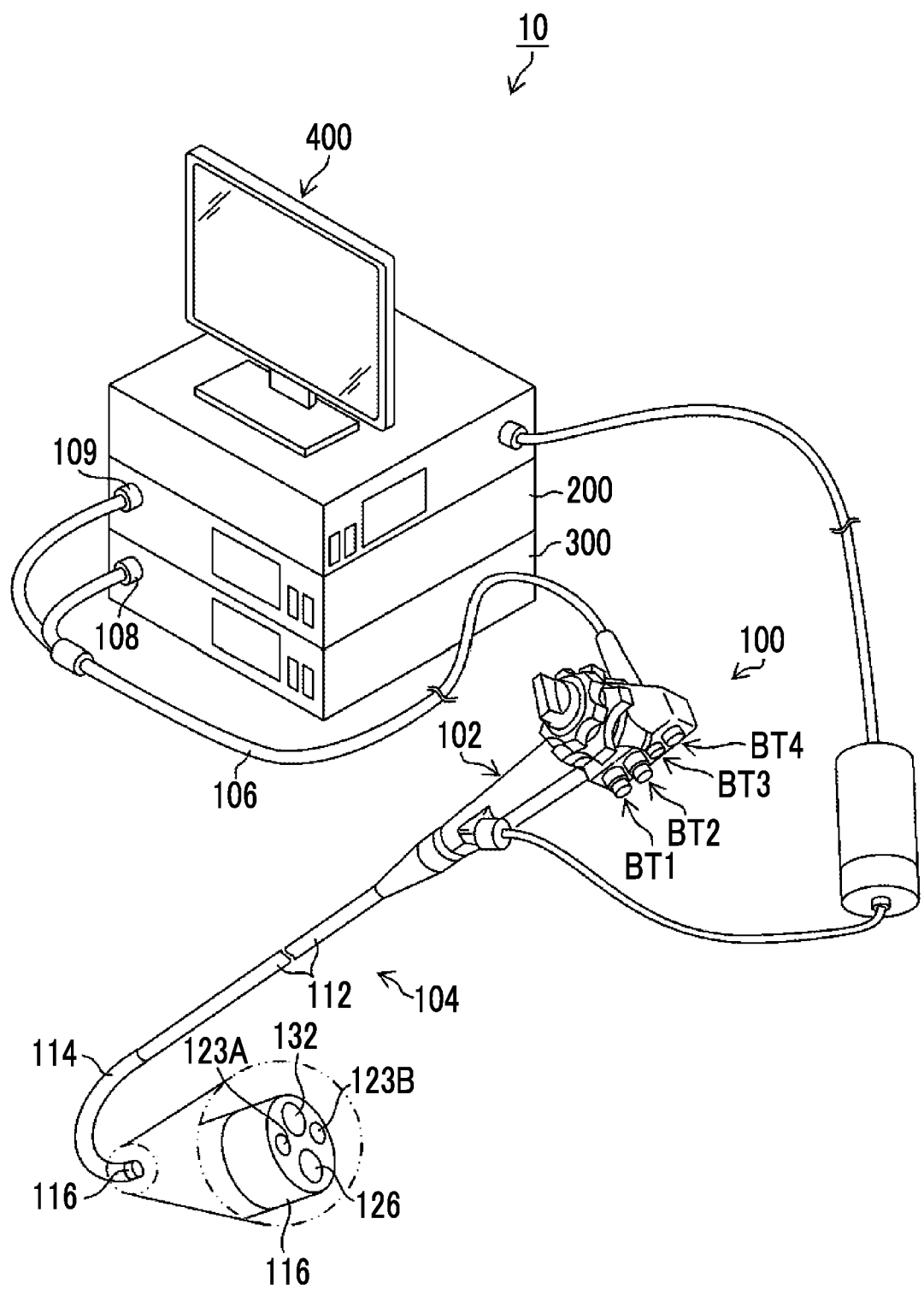
FIG. 1 is a diagram showing an appearance of an endoscope system according to a first embodiment.
Figure 2:
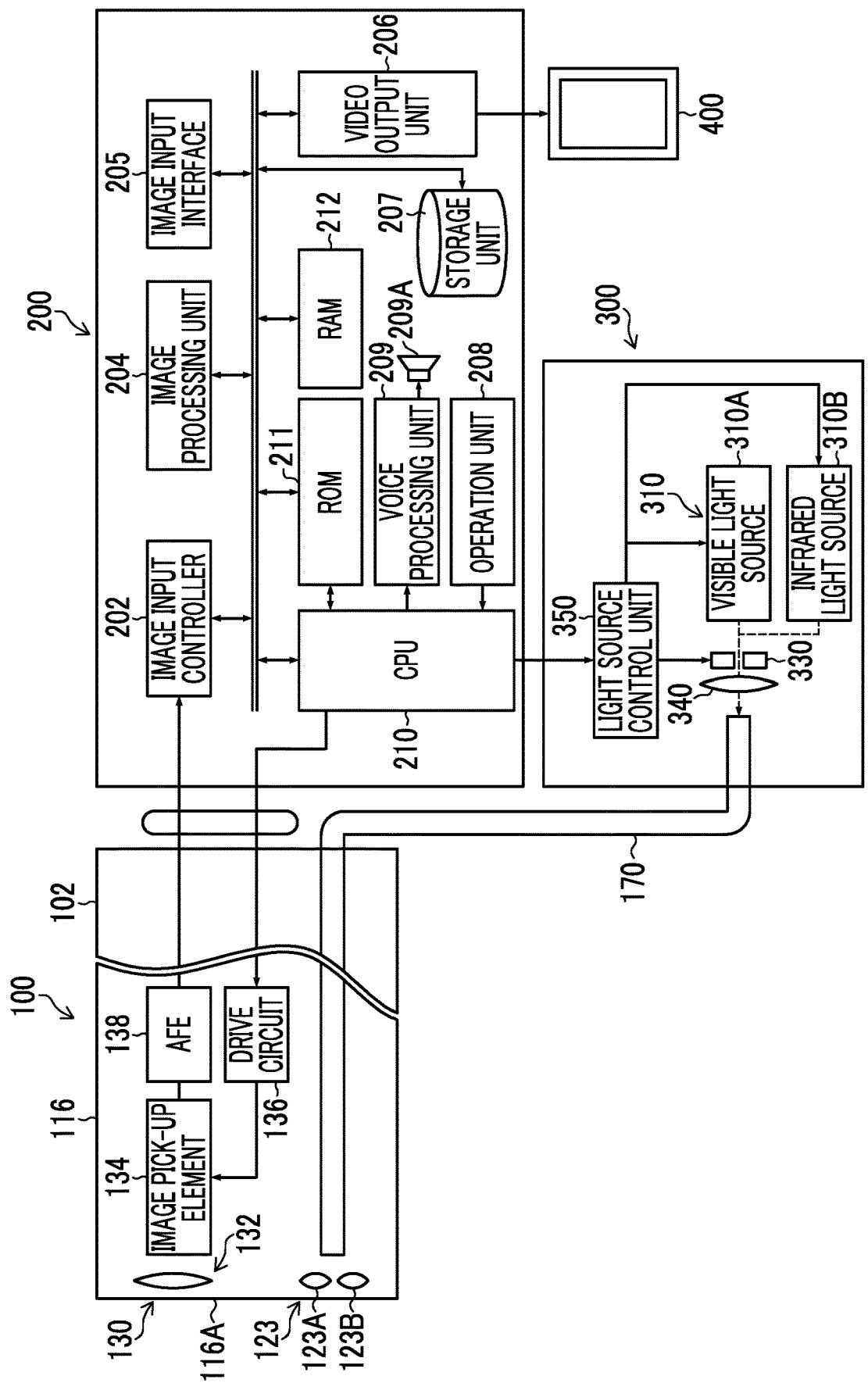
FIG. 2 is a block diagram showing a configuration of the endoscope system.

FIG. 1 is a diagram showing an appearance of an endoscope system 10 (diagnosis support system, diagnosis support apparatus, endoscope system, processor, medical image processing device) according to a first embodiment, and FIG. 2 is a block diagram showing a main configuration of the endoscope system 10. As shown in FIGS. 1 and 2, the endoscope system 10 includes an endoscope body 100 (endoscope), a processor 200 (processor, medical image processing device), a light source device 300, and a monitor 400 (display device).

<Configuration of Endoscope Body>

The endoscope body 100 comprises a hand operation part 102 (operation part) and an insertion part 104 (insertion part) connected to the hand operation part 102. An operator (user) grips and operates the hand operation part 102, inserts the insertion part 104 into an object to be examined (living body), and observes the object to be examined. Further, the hand operation part 102 is provided with an air/water supply button BT1, a suction button BT2, a function button BT3 to which various functions are assigned, and an imaging button BT4 that receives an imaging instruction operation. The insertion part 104 includes a soft portion 112 (soft portion), a bendable portion 114 (bendable portion), and a hard distal end portion 116 (hard distal end portion) that are arranged in this order from the hand operation part 102. That is, the bendable portion 114 is connected to the proximal end side of the hard distal end portion 116, and the soft portion 112 is connected to the proximal end side of the bendable portion 114. The hand operation part 102 is connected to the proximal end side of the insertion part 104. In a case where a user operates the hand operation part 102, the user can bend the bendable portion 114 to vertically and laterally change the direction of the hard distal end portion 116. The hard distal end portion 116 is provided with an imaging optical system 130 (image-for-medical-use acquisition unit, image-for-medical-use capturing unit, imaging device, image pick-up unit), an illumination unit 123, a forceps port 126, and the like (refer to FIGS. 1 to 3).

At the time of observation and treatment, either visible light or infrared light, or both visible light and infrared light can be applied from illumination lenses 123A and 123B of the illumination unit 123 by the operation of an operation unit 208 (refer to FIG. 2). Further, cleaning water is ejected from a water supply nozzle (not shown) by the operation of the air/water supply button BT1, so that an imaging lens 132 (imaging lens) of the imaging optical system 130 and the illumination lenses 123A and 123B can be cleaned. A pipe line (not shown) communicates with the forceps port 126 that is open at the hard distal end portion 116, and a treatment tool (not shown) for the removal of a tumor or the like is inserted into the pipe line and is appropriately moved forwards and backwards to perform necessary treatment on an object to be examined.

Figure 3:
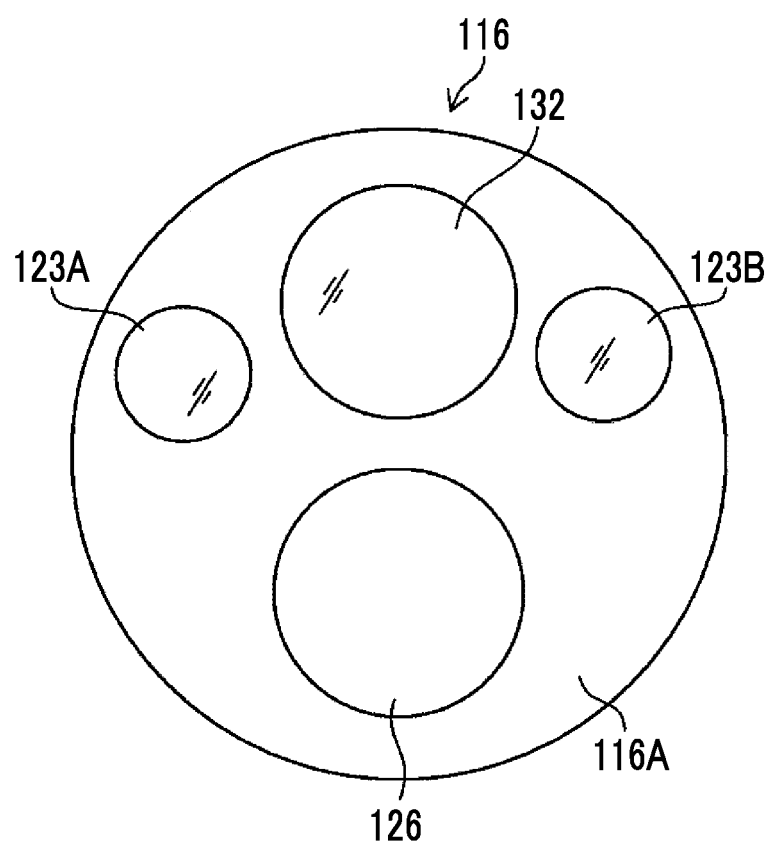
FIG. 3 is a diagram showing a configuration of a hard distal end portion of an endoscope.

As shown in FIGS. 1 to 3, the imaging lens 132 (image pick-up unit) is provided on a distal end-side end face 116A of the hard distal end portion 116. A complementary-metal-oxide-semiconductor (CMOS) type image pick-up element 134 (image pick-up element, image pick-up unit, imaging device, medical image acquisition unit, image sensor), a drive circuit 136, and an analog front end (AFE) 138 are provided in the back of the imaging lens 132, and image signals are output by these elements. The image pick-up element 134 is a color image pick-up element, and comprises a plurality of pixels formed of a plurality of light-receiving elements that are arranged in a matrix form (two-dimensionally arrayed) so as to have a specific pattern array (Bayer array, X-Trans (registered trademark) array, honeycomb array, or the like). Each pixel of the image pick-up element 134 includes a microlens, a red (R), green (G), or blue (B) color filter, and a photoelectric conversion part (photodiode or the like). The imaging optical system 130 also can generate a color image from pixel signals corresponding to three colors of red, green, and blue, and also can generate an image from pixel signals corresponding to any one color or two colors of red, green, and blue. A case where the image pick-up element 134 is a CMOS type image pick-up element has been described in the first embodiment, but the image pick-up element 134 may be a charge-coupled-device (CCD) type image pick-up element.

The optical image of an object to be examined (tumor area or lesion area) is formed on the light-receiving surface (image pick-up surface) of the image pick-up element 134 by the imaging lens 132 and is converted into electrical signals, and the electrical signals are output to the processor 200 through a signal cable (not shown) and are converted into video signals. Accordingly, an observation image is displayed on the monitor 400 connected to the processor 200.

Further, the illumination lens 123A (for visible light) and the illumination lens 123B (for infrared light) of the illumination unit 123 are provided on the distal end-side end face 116A of the hard distal end portion 116 so as to be adjacent to the imaging lens 132. An emitting end of a light guide 170 to be described below is provided in the back of the illumination lenses 123A and 123B; the light guide 170 is inserted into the insertion part 104, the hand operation part 102, and a universal cable 106; and an incident end of the light guide 170 is disposed in a light guide connector 108.

<Configuration of Light Source Device>

As shown in FIG. 2, the light source device 300 includes a light source 310 for illumination, a stop 330, a condenser lens 340, a light source control unit 350, and the like, and causes illumination light (visible light or infrared light) to be incident on the light guide 170. The light source 310 comprises a visible light source 310A and an infrared light source 310B, and can apply either visible light or infrared light or both visible light and infrared light. The illuminance of illumination light applied by the visible light source 310A and the infrared light source 310B is controlled by the light source control unit 350, so that the illuminance of illumination light can be lowered or illumination can be stopped as necessary.

<Wavelength Range of Light Source>

The light source 310 (visible light source 310A) may be a light source that generates light in a white-light wavelength range or generates light in a plurality of wavelength ranges as light in a white-light wavelength range, and may be a light source that generates light in a specific wavelength range narrower than the white-light wavelength range. The specific wavelength range may be a blue-light wavelength range or a green-light wavelength range of a visible-light wavelength range or a red-light wavelength range of a visible-light wavelength range. In a case where the specific wavelength range is a blue-light wavelength range or a green-light wavelength range of a visible-light wavelength range, the specific wavelength range may include a wavelength range of 390 nm to 450 nm or 530 nm to 550 nm, and light in the specific wavelength range may have a peak wavelength in a wavelength range of 390 nm to 450 nm or 530 nm to 550 nm. Further, in a case where the specific wavelength range is a red-light wavelength range of a visible-light wavelength range, the specific wavelength range may include a wavelength range of 585 nm to 615 nm or 610 nm to 730 nm, and light in the specific wavelength range may have a peak wavelength in a wavelength range of 585 nm to 615 nm or 610 nm to 730 nm.

Light in the above-described specific wavelength range may include a wavelength range where a light absorption coefficient in oxyhemoglobin is different from that in reduced hemoglobin, and may have a peak wavelength in a wavelength range where a light absorption coefficient in oxyhemoglobin is different from that in reduced hemoglobin. In this case, the specific wavelength range may include a wavelength range of 400±10 nm, 440±10 nm, 470±10 nm, or 600 nm to 750 nm, and light in the specific wavelength range may have a peak wavelength in a wavelength range of 400±10 nm, 440±10 nm, 470±10 nm, or 600 nm to 750 nm.

Further, light generated by the light source 310 (infrared light source 310B) may have a wavelength range of 790 nm to 820 nm or 905 nm to 970 nm, and may have a peak wavelength in a wavelength range of 790 nm to 820 nm or 905 nm to 970 nm.

Further, the light source 310 may comprise a light source that applies excitation light having a peak wavelength in a wavelength range of 390 nm to 470 nm. In this case, an image for medical use (in-vivo image), which includes information about the fluorescence of a fluorescent material present in an object to be examined (living body), can be acquired. A pigment for a fluorescence method (fluorescein, acridine orange, or the like) may be used to acquire a fluorescence image.

It is preferable that the type (laser light source, xenon light source, light-emitting-diode (LED) light source, and the like) and wavelength of the light source 310, the presence or absence of a filter, and the like are determined according to the type of a subject, the purpose of observation, and the like. Further, it is preferable that the wavelengths of illumination light are combined and/or switched according to the type of a subject, the purpose of observation, and the like at the time of observation. In a case where the wavelengths are to be switched, for example, a disc-shaped filter (rotary color filter) provided with filters, which are disposed in front of a light source and transmit or block light having specific wavelengths, may be rotated to switch the wavelength of light to be applied.

Furthermore, an image pick-up element, which is used to embody the invention, is not limited to a color image pick-up element where a color filter is provided for each pixel as with the image pick-up element 134, and may be a monochromatic image pick-up element. In a case where a monochromatic image pick-up element is used, image pick-up can be performed in order of surface (in order of color) while the wavelengths of illumination light are sequentially switched. For example, the wavelengths of illumination light to be emitted may be sequentially switched among purple, blue, green, and red; and broadband light (white light) may be applied and the wavelengths of illumination light to be emitted may be switched by the rotary color filter (red, green, blue, and the like). Moreover, one or a plurality of narrow-band lights (green light, blue light, and the like) may be applied and the wavelengths of illumination light to be emitted may be switched by the rotary color filter (green, blue, and the like). The narrow-band lights may be infrared lights having two or more different wavelengths.

The light guide connector 108 (refer to FIG. 1) is connected to the light source device 300, so that illumination light applied from the light source device 300 is transmitted to the illumination lenses 123A and 123B through the light guide 170 and is applied to an observation range from the illumination lenses 123A and 123B.

<Configuration of Processor>

The configuration of the processor 200 will be described with reference to FIG. 2. The image signals output from the endoscope body 100 are input to the processor 200 through an image input controller 202 and an image input interface 205, and the processor 200 performs necessary image processing on the image signals by an image processing unit 204 and outputs the resultant signals through a video output unit 206. Accordingly, an observation image (in-vivo image) is displayed on the monitor 400 (display device). These kinds of processing are performed under the control of a central processing unit (CPU) 210. That is, the CPU 210 has functions as an image-for-medical-use acquisition unit, a display control unit, a first detection unit, a second detection unit, a first detection information assigning unit, a second detection information assigning unit, a region-of-interest determination unit, and a feature designation unit. The storage unit 207 stores an image of a subject (image for medical use, captured image) and detection information (first detection information and second detection information) to be described below. A voice processing unit 209 outputs warning messages (voice) or the like at the time of setting display conditions, from a speaker 209A by the control of the CPU 210 and the image processing unit 204.

Furthermore, a read only memory (ROM) 211 is a non-volatile storage element (non-temporary recording medium), and computer-readable codes of a program causing the CPU 210 and/or the image processing unit 204 to execute a diagnosis support method according to an embodiment of the invention, are stored in the ROM 211. A random access memory (RAM) 212 is a storage element for temporary storage at the time of various kinds of processing, and can also be used as a buffer at the time of acquisition of an image.

<Functions of Image Processing Unit>

Figure 4:
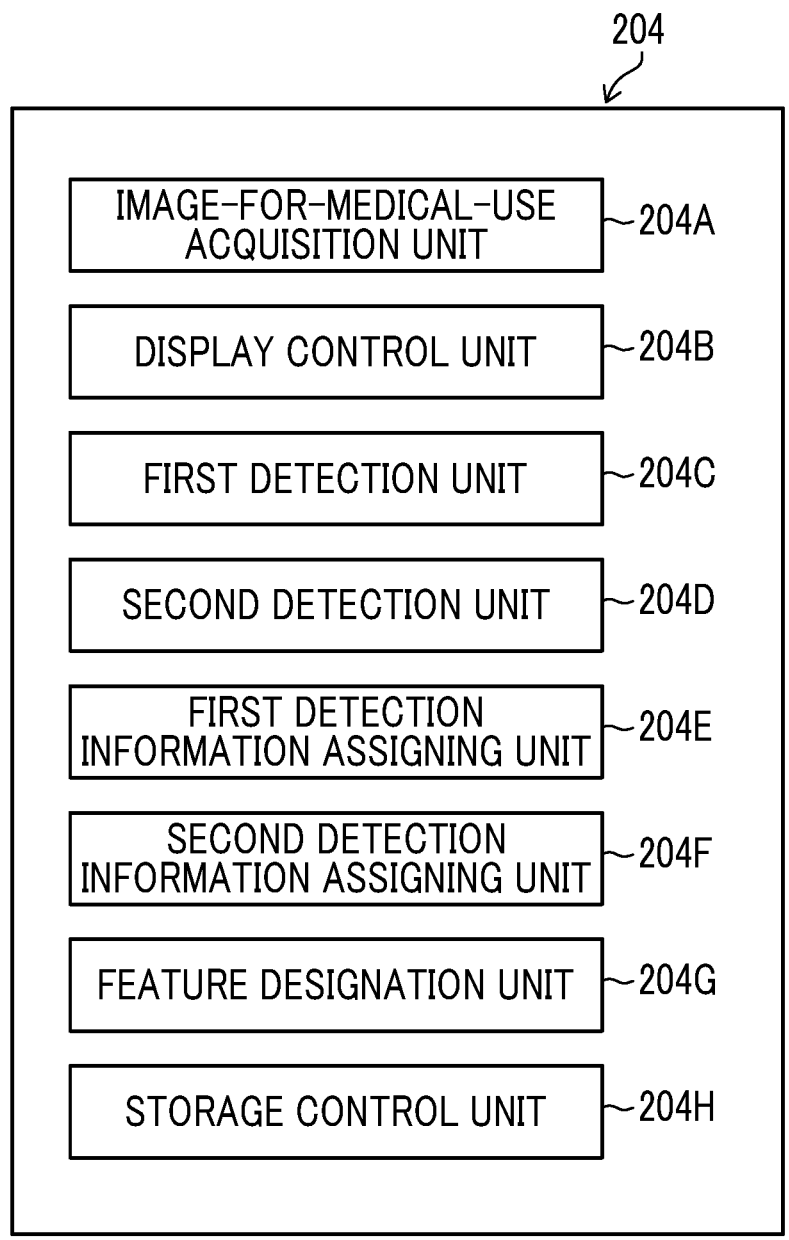
FIG. 4 is a diagram showing a functional configuration of an image processing unit.

FIG. 4 is a diagram showing the functional configuration of the image processing unit 204 (medical image acquisition unit, medical image analysis processing unit, medical image analysis result acquisition unit). The image processing unit 204 has an image-for-medical-use acquisition unit 204A, a display control unit 204B, a first detection unit 204C, a second detection unit 204D, a first detection information assigning unit 204E, a second detection information assigning unit 204F, a feature designation unit 204G, and a storage control unit 204H. The first detection unit 204C and the second detection unit 204D also operate as the medical image analysis processing unit.

The image processing unit 204 may comprise a special light image acquisition unit that acquires a special light image including information about the specific wavelength range on the basis of a normal light image obtained from the application of light in a white-light wavelength range or light in a plurality of wavelength ranges as the light in a white-light wavelength range. In this case, a signal in the specific wavelength range can be obtained from an arithmetic operation based on color information about RGB (R: red, G: green, and B: blue) or CMY (C: cyan, M: magenta, and Y: yellow) included in the normal light image.

Further, the image processing unit 204 may comprise a feature-quantity-image generation unit generating a feature quantity image from an arithmetic operation based on at least one of a normal light image that is obtained from the application of light in a white-light wavelength range or light in a plurality of wavelength ranges as the light in a white-light wavelength range or a special light image that is obtained from the application of light in a specific wavelength range, and may acquire and display a feature quantity image as an image for medical use (medical image).

The processing to be fulfilled by these functions of the image processing unit 204 will be described in detail below. The processing to be fulfilled by these functions is performed under the control of the CPU 210.

The functions of the above-described image processing unit 204 can be fulfilled using various processors. The various processors include a central processing unit (CPU) that is a general-purpose processor fulfilling various functions by executing software (program), for example.

Further, the above-described various processors also include a programmable logic device (PLD) that is a processor of which the circuit configuration can be changed after manufacture, such as a field programmable gate array (FPGA). Furthermore, the above-described various processors also include dedicated electrical circuitry, which is a processor having a circuit configuration designed exclusively to execute specific processing, such as an application specific integrated circuit (ASIC).

The functions of each unit may be fulfilled by one processor, or may be fulfilled by a plurality of processors in combination. Further, a plurality of functions may be fulfilled by one processor. As an example where a plurality of functions are formed by one processor, first, there is an aspect where one processor is formed of a combination of one or more CPUs and software as typified by a computer, such as a client or a server, and this processor fulfils a plurality of functions. Second, there is an aspect where a processor fulfilling the functions of the entire system by one integrated circuit (IC) chip as typified by System On Chip (SoC) or the like is used. In this way, various functions are formed using one or more of the above-described various processors as hardware structures.

Furthermore, the hardware structures of these various processors are more specifically electrical circuitry where circuit elements, such as semiconductor elements, are combined.

In a case where the above-described processor (or electrical circuitry) is to execute software (program), computer-readable codes of the software to be executed (including the program for causing the diagnosis support method according to an embodiment of the invention to be executed) are stored in a non-temporary recording medium, such as the ROM 211 (refer to FIG. 2), and the processor refers to the software. In a case where processing is to be performed using software, for example, the RAM 212 (refer to FIG. 2) is used as a temporary storage region and the processor or electrical circuitry can also refer to data stored in, for example, an electronically erasable and programmable read only memory (EEPROM). In FIG. 4, illustration of devices such as the EEPROM and the like is omitted.

<Configuration of Operation Unit>

The processor 200 comprises the operation unit 208. The operation unit 208 comprises an operation mode setting switch (not shown) and the like, and can operate the application of visible light and/or infrared light. Further, the operation unit 208 includes a keyboard and a mouse (which are not shown), and a user can perform a setting operation for the imaging conditions and the display conditions via the devices (which will be described below). Setting of the operation mode may be performed by assigning an operation mode setting function to the function button BT3 (refer to FIG. 1) of the hand operation part 102 as described above.

<Configuration of Storage Unit>

Figures 5, 6:
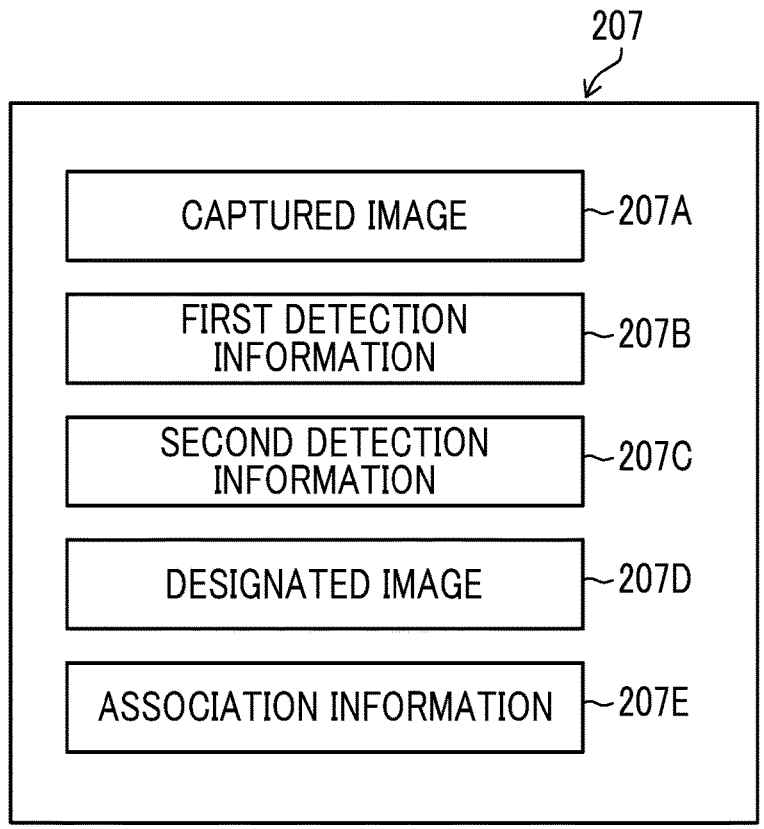
FIG. 5 is a diagram showing an image and information stored in a storage unit.
FIG. 6 is a diagram showing an aspect of correspondence between an image for medical use, first detection information, and second detection information.

The storage unit 207 (recording device) is formed by a non-temporary recording medium such as a compact disk (CD), a digital versatile disk (DVD), a hard disk, and various semiconductor memories, and stores information and images shown in FIG. 5 in association with each other. As shown in FIG. 5, the storage unit 207 stores a captured image 207A, first detection information 207B, second detection information 207C, a designated image 207D, and association information 207E. The captured image 207A, the designated image 207D, and the first detection information 207B and/or the second detection information 207C are recorded to correspond to each other by the association information 207E as shown in FIG. 6, for example. In FIG.

6, "i101" and the like are identification information of images. The captured image 207A, the designated image 207D, the first detection information 207B, and the second detection information 207C are displayed on the monitor 400 by an operation, which is performed through the operation unit 208, and the control of the CPU 210 and/or the image processing unit 204.

The storage unit 207 (recording device) may store analysis results regarding any one or both of a notable region (region of interest) as a region to be notable included in the image for medical use (medical image) and the presence or absence of the object to be notable. In this case, the image processing unit 204 (medical image analysis processing unit, medical image analysis result acquisition unit) can display the analysis results on the monitor 400 by acquiring the analysis results from the storage unit 207.

<Configuration of Display Device>

Figure 9:
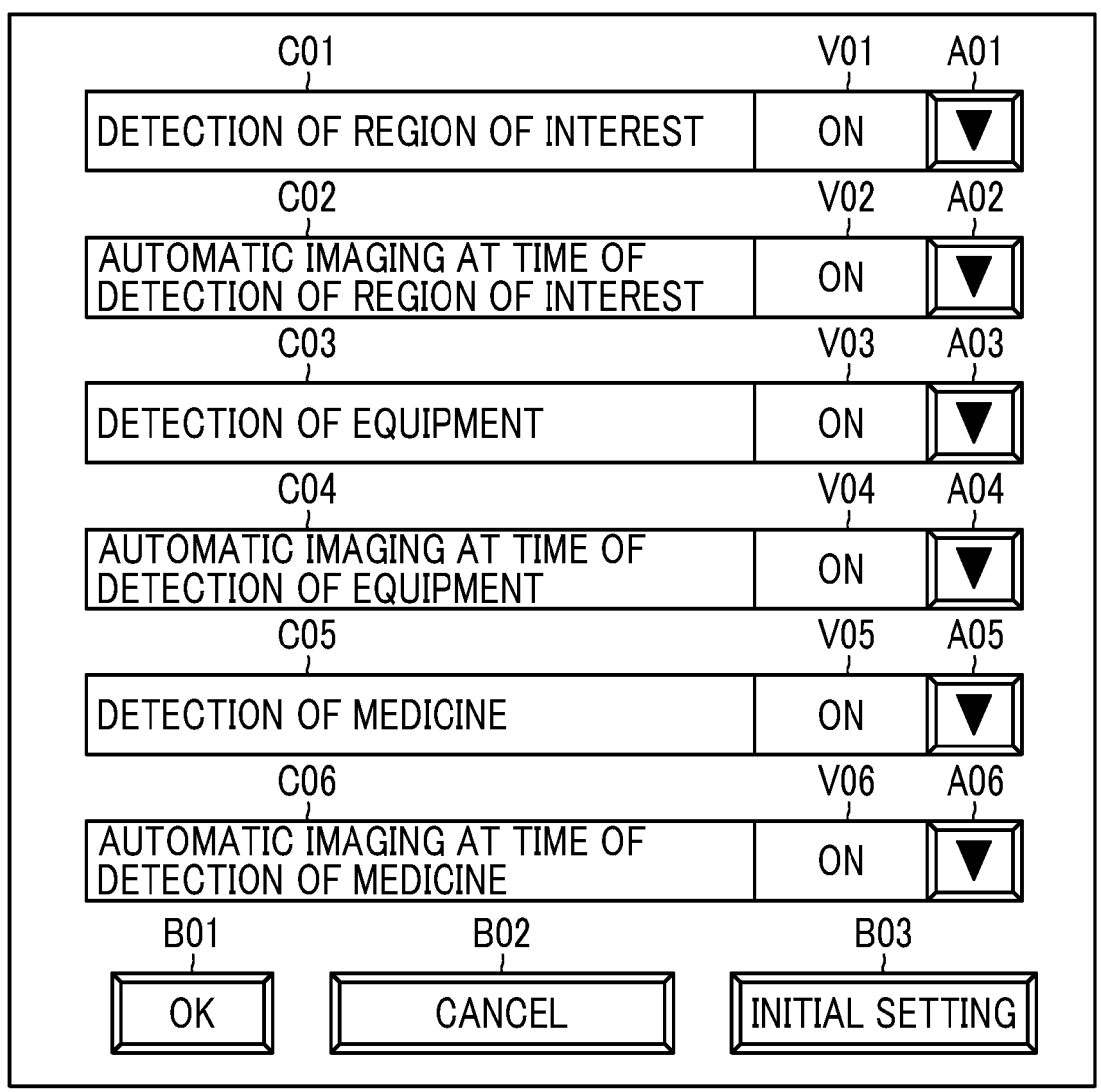
FIG. 9 is a diagram showing an example of an imaging condition setting screen.
Figure 11:
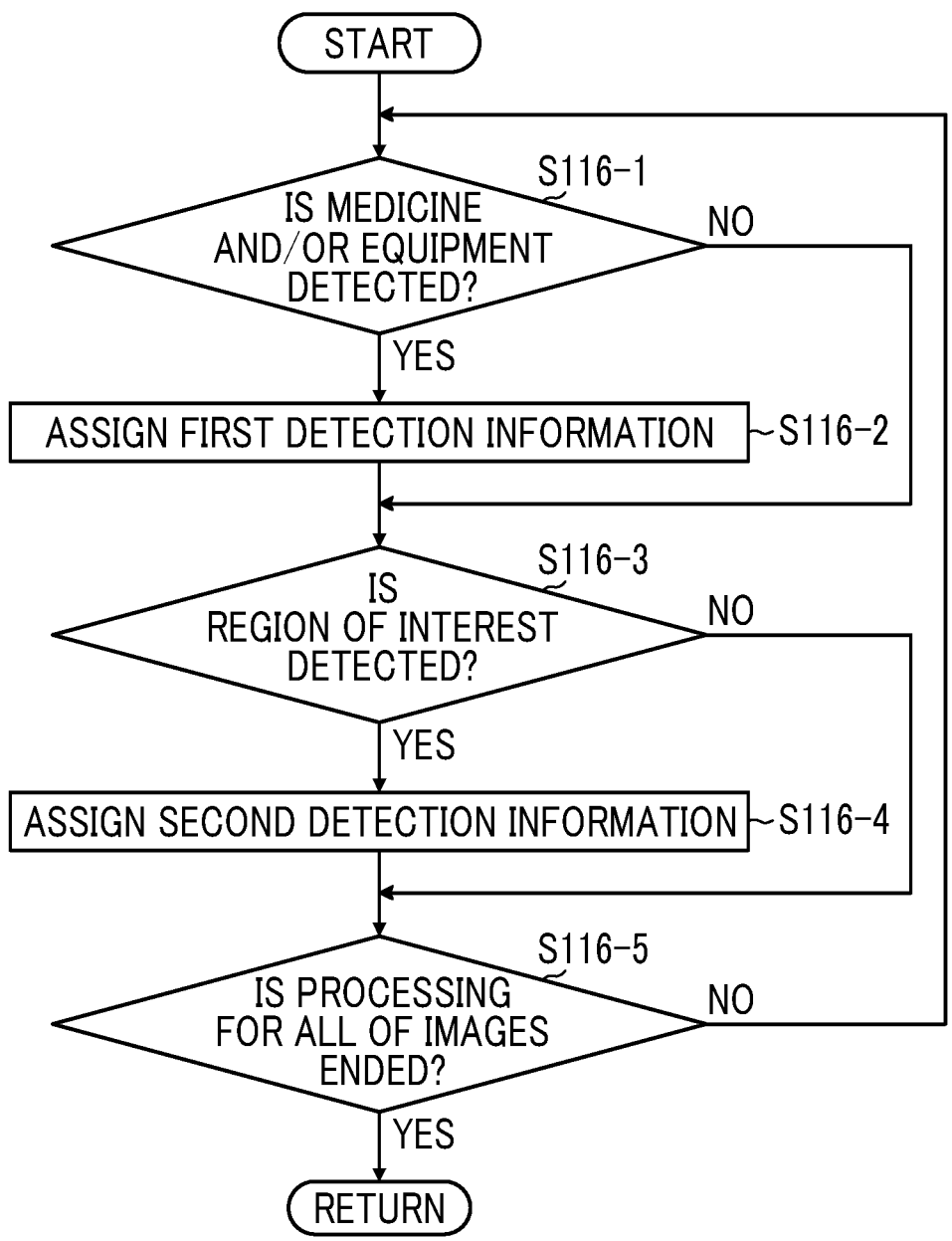
FIG. 11 is a flowchart showing processing of assigning the first detection information and the second detection information.

The monitor 400 (display device) displays the captured image (image for medical use), the imaging condition setting screen, the display condition setting screen, the first detection information, the second detection information, and the like by the operation, which is performed through the operation unit 208, and the control of the CPU 210 and/or the image processing unit 204 (refer to FIGS. 9 to 11). Further, the monitor 400 includes a touch panel (not shown) that is used to perform an operation for setting an imaging condition and/or an operation for setting a display condition.

<Processing of Diagnosis Support Method>

Figure 7:
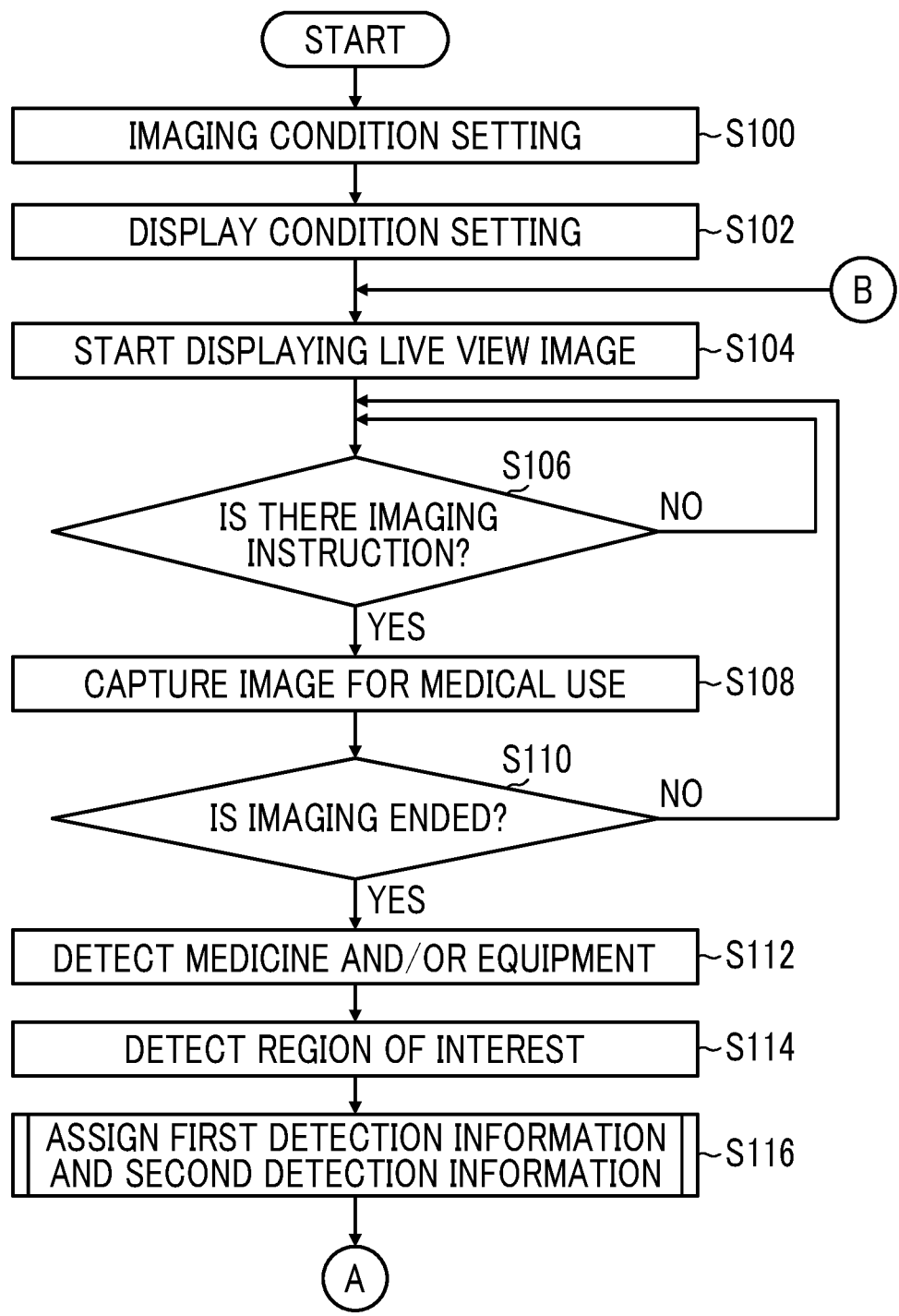
FIG. 7 is a flowchart showing processing of a diagnosis support method.
Figure 8:
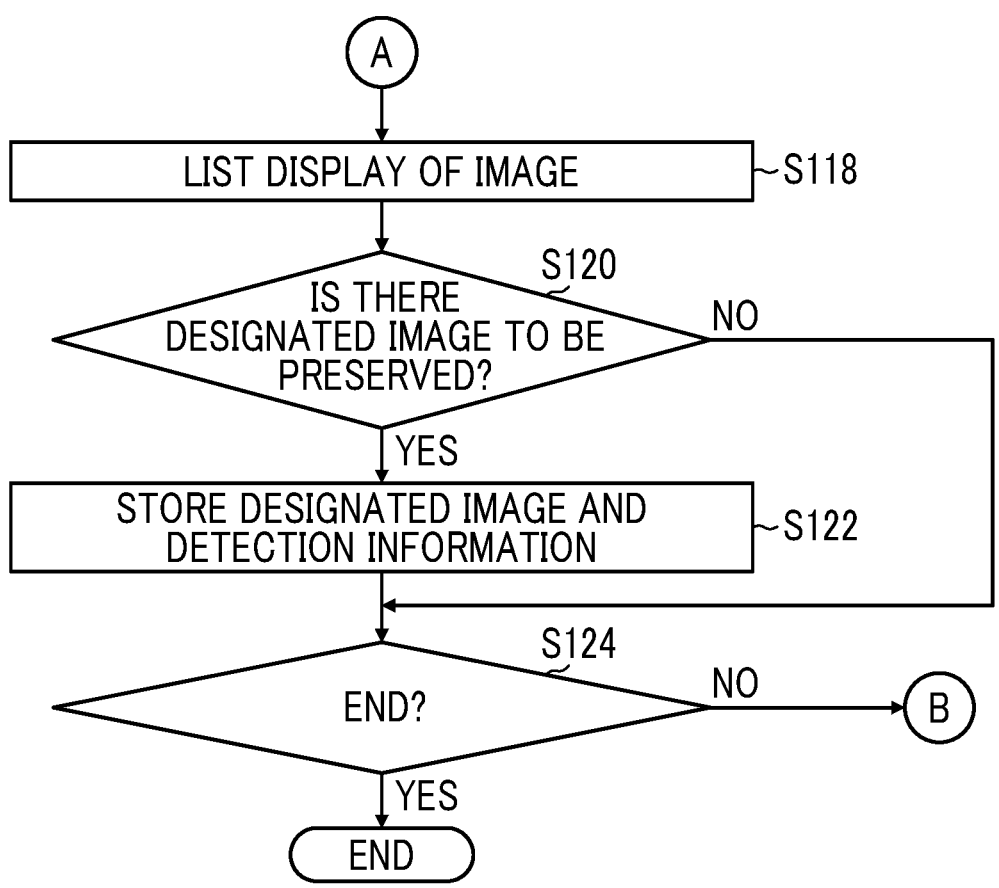
FIG. 8 is another flowchart showing the processing of the diagnosis support method.

A diagnosis support method for an object to be examined, using the endoscope system 10 will be described. FIGS. 7 and 8 are flowcharts showing the processing of the diagnosis support method according to the first embodiment.

<Setting of Imaging Condition>

In the flowcharts of FIGS. 7 and 8, setting of the imaging condition and the display condition is performed on the basis of the user's instruction prior to the imaging (steps S100 and S102). However, the setting may be performed during the imaging or after the imaging. FIG. 9 is a diagram showing an example of the imaging condition setting screen. In FIG. 9, regarding each item of the imaging conditions, a condition name (regions C01 to C06), the contents of the setting condition (regions V01 to V06), and a pull-down button (buttons A01 to A06) are shown. A button B01 is a button for confirming the display conditions, a button B02 is a button for cancelling the condition change, a button B03 is a button for returning the conditions to initial setting, and the buttons B01 to B03 are provided in a lower portion of the screen. The screen in FIG. 9 is displayed on the monitor 400, and the display condition can be set by the user's operation via the touch panel of the monitor 400 and/or the keyboard and/or mouse of the operation unit 208.

The regions C01 and V01 indicate "whether to detect a region of interest from the acquired image", and ON (detecting) or OFF (not detecting) can be designated through the button A01. In a case where ON is selected, a region of interest (lesion region, lesion candidate region, and the like; referred to as a notable region) is detected by the image processing unit 204 (second detection unit 204D). The regions C02 and V02 indicate "whether to automatically perform imaging in a case where a region of interest is detected", and ON (automatically imaging) or OFF (not automatically imaging) can be designated by an operation through the button A02. In a case where ON is selected, the image-for-medical-use acquisition unit 204A (image-for-medical-use acquisition unit) controls the imaging optical system 130 to perform imaging according to the detection of the region of interest. The regions C03 and V03 indicate "whether to detect equipment from the acquired image", and ON (detecting) or OFF (not detecting) can be selected by an operation through the button A03. The "equipment" includes a treatment tool (for example, forceps, needle, clip, tube, and the like) for performing biopsies, excision, and the like on an object to be examined, and can be inserted into the object to be examined through the forceps port 126. The regions C04 and V04 indicate "whether to automatically perform imaging in a case where equipment is detected", and ON (automatically imaging) or OFF (not automatically imaging) can be selected by a selection operation through the button A04. In a case where ON is selected, the image-for-medical-use acquisition unit 204A controls the imaging optical system 130 to perform imaging according to the detection of the equipment by the first detection unit 204C (first detection unit).

The regions C05 and V05 indicate "whether to detect a medicine from the acquired image", and ON (detecting) or OFF (not detecting) can be selected by an operation through the button A05. The "medicine" includes a pigment and a dye for observing the shape, unevenness, and the like of a lesion. The regions C06 and V06 indicate "whether to automatically perform imaging in a case where a medicine is detected", and ON (automatically imaging) or OFF (not automatically imaging) can be selected by a selection operation through the button A06. In a case where ON is selected, the image-for-medical-use acquisition unit 204A controls the imaging optical system 130 to perform imaging according to the detection of the medicine by the first detection unit 204C.

Since it is possible to perform imaging with desired conditions by setting the conditions through such a setting screen, it is possible for a user to efficiently perform diagnosis, report creation, and the like. The condition setting in FIG. 9 is an example, and addition or deletion of a condition, or a change of the contents of a condition may be performed.

<Setting of Display Condition>

FIG. 10 is a diagram showing an example of a list display condition setting screen. Regions C07 and V07 indicate a display form of the detected medicine, and character display, symbol display or the like of the name can be designated by a selection operation through a button A07. Regions C08 and V08 indicate a display form of the detected equipment, and name display, procedure name display, or the like can be designated by a selection operation through a button A08. Regions C09 and V09 indicate a distinguishable display form of the image from which the region of interest is detected, and frame (figure) addition, character and/or numerical number addition, color addition, or the like can be designated by a selection operation through a button A09. Regions C10 and V10 indicate "whether to display only the image from which the region of interest is detected", and ON or OFF can be designated by a selection operation through a button A10. Regions C11 and V11 indicate "whether to display the image for each type of the medicine", and ON or OFF can be designated by a selection operation through a button A11. Regions C12 and V12 indicate "whether to display only the image for a specific type of the medicine", and ON or OFF can be designated by a selection operation through a button A12.

Since it is possible to display the image with desired conditions by setting the conditions through such a setting screen, it is possible for a user to efficiently perform diagnosis, report creation, and the like.

In a case where setting of the imaging condition and the display condition in steps S100 and S102 is ended and the insertion part 104 of the endoscope body 100 is inserted into an object to be examined, acquisition of live view images by the imaging optical system 130 and the image processing unit 204 (image-for-medical-use acquisition unit 204A) and displaying the live view images on the monitor 400 are started (step S104). In this manner, a user can observe an aspect inside an object to be examined. In a case where the user performs an insertion operation and a bending operation of the insertion part 104 to direct the hard distal end portion 116 toward a desired direction, and operates the imaging button BT4, the image-for-medical-use acquisition unit 204A receives an imaging instruction operation. In this manner, the determination (presence or absence of imaging instruction) in step S106 is affirmative and the processing proceeds to step S108 (image-for-medical-use acquisition step), and an image for medical use (static image; medical image, endoscopic image) is acquired by the imaging optical system 130 (image-for-medical-use capturing unit, imaging device, medical image acquisition unit) and the image-for-medical-use acquisition unit 204A (imaging control unit, medical image acquisition unit). Further, even in a case where there is no operation of the imaging button BT4, in a case where automatic imaging (refer to FIG. 9) according to the detection of the region of interest, the detection of the medicine, and the like is ON, when the setting conditions are satisfied, an imaging instruction is issued by the image-for-medical-use acquisition unit 204A (YES in step S106) and the image for medical use is captured (step S108). The image captured in step S108 may be a static image or a video, and in the following description, it is assumed that a static image is captured.

In a case where the image for medical use is acquired in step S108, the acquired image for medical use is stored in the storage unit 207. The image-for-medical-use acquisition unit 204A continues to acquire and store an image for medical use until the end of imaging (YES in step S110), and thus acquires a plurality of images for medical use. In case of the end of imaging, the image-for-medical-use acquisition unit 204A ends the acquisition and the display of the live view image.

<Detection of Medicine and/or Equipment>

In a case where a plurality of images for medical use are acquired by the processing until step S110, the image processing unit 204 (first detection unit 204C) detects a medicine and/or equipment from the plurality of acquired images for medical use by image recognition (step S112: first detection step). Further, the second detection unit 204D (second detection unit) detects a region of interest from the plurality of acquired images for medical use by image recognition (step S114: second detection step). Either step S112 or step S114 may be performed first.

<Detection Method of Medicine>

The detection of the medicine (including pigments and dyes) in step S112 can be performed on the basis of a color feature quantity by using the above-described method disclosed in JP2016-062488A, for example. Specifically, the image processing unit 204 (first detection unit 204C) excludes dark pixels and halation pixels on the basis of pixel values of red (R), green (G), and blue (B) in each pixel of the image for medical use, calculates the color feature quantity (G/R, B/G) for each of the pixels which are not excluded, and calculates an average value of the color feature quantities for each small block obtained by dividing the image for medical use. The average value for R/G is set as μGR, the average value for B/G is set as μBG, and in a case where μGR and μBG are plotted, the plotting results show different distributions depending on the individual medicines (pigments, dyes, or the like). Accordingly, it is possible to discriminate the medicine used in the acquired image for medical use by comparing the plotting result (positions in feature space) of the medicine as a detection target with the distributions for the individual medicines. The contents of the procedure or the treatment performed using the type of the medicine and the detection result (for example, type and name of the medicine) are associated with each other in advance, and may be included in the detection information (first detection information) to be assigned to the image.

The detection of the medicine may be performed by using the results of machine learning (deep learning or the like) (refer to the description described below for the detection of the region of interest).

<Detection Method of Equipment>

The detection of equipment in step S112 can be performed by using the above-described method disclosed in JP2016-062488A. Specifically, the endoscopic image at the time of inserting each treatment tool into a forceps channel (pipe line (not shown) communicating with the forceps port 126) is set as a template image and the first detection unit 204C collates the template image with the endoscopic image at the time of inspection to detect which treatment tool is used. As the template image, a plurality of images with different forceps channel directions, protrusion lengths, and open/close states are prepared for each treatment tool. For an asymmetric treatment tool of which the shape is changed on the image by rotation, a plurality of images with different rotation angles are prepared.

In order to detect a treatment tool from the endoscopic image, the first detection unit 204C detects an edge from the endoscopic image. As the image for the edge detection, an R image (image generated from a pixel signal of a red pixel) or a G image (image generated from a pixel signal of a green pixel) is used. In a case where the treatment tool sheath is red, the G image is preferably used. A line shape is detected from the edge image by using the template matching, the Hough transform, or the like, and a degree of coincidence is calculated by collating the detected line shape with the template image. The treatment tool of the template image having the highest degree of coincidence is set as the detection result. The contents of the procedure or the treatment performed using the equipment and the detection result (for example, type and name of the equipment) are associated with each other in advance, and may be included in the detection information (first detection information) to be assigned to the image.

Similarly to the detection of the medicine, the detection of the equipment may be performed by using the results of machine learning (deep learning or the like) (refer to the description described below for the detection of the region of interest).

<Detection Method of Region of Interest>

The detection of the region of interest in step S114 can be performed by providing, for example, a known computer aided diagnosis (CAD) system to the second detection unit 204D. Specifically, it is possible to extract the region of interest (notable region which is a region to be notable) and the presence or absence of a target (target to be notable) in the region of interest on the basis of, for example, a feature quantity of pixels of the image for medical use. In this case, the second detection unit 204D divides a detection target image into a plurality of rectangular regions, and sets each divided rectangular region as the local region. The second detection unit 204D calculates the feature quantity (for example, hue) of pixels in the local region, for each of the local regions of the detection target image; and determines the local region having specific hue among the local regions, as the region of interest.

The detection of the region of interest may be performed by using the results of machine learning (deep learning or the like). For example, whenever a new image is stored in the storage unit 207 (or whenever a new image is captured), the second detection unit 204D analyzes whether the region of interest is included in the image by performing image analysis processing using deep learning on the basis of a deep learning algorithm. The deep learning algorithm is an algorithm for recognizing whether the region of interest is included in the image through a known convolutional neural network method, that is, through repetition of a convolutional layer and a pooling layer, a fully connected layer, and an output layer. "Whether to perform such machine learning" and/or "whether to use the learning results" may be set through a condition setting screen as shown in FIG. 9.

In step S114, the type, number, shape, size, and the like of the region of interest can be the detection target. Further, the detection of the medicine and/or equipment and the detection of the region of interest are performed after the end of capturing all the images (YES in step S110) in FIG. 7, but the detection of the medicine and/or equipment and the detection of the region of interest may be performed whenever an image is captured (between step S108 and step S110).

<Assigning Detection Information>

In a case where the medicine and/or equipment and the region of interest are detected in steps S112 and 114, the image processing unit 204 (first detection information assigning unit 204E and second detection information assigning unit 204F) assigns the first detection information and the second detection information to the captured image on the basis of the detection result (step S116: first detection information assigning step, and second detection information assigning step). Assigning the detection information will be described with reference to FIG. 11.

The first detection information assigning unit 204E (first detection information assigning unit) determines whether the first detection unit 204C has detected the medicine and/or equipment (step S116-1). In a case where the medicine and/or equipment is detected (YES in step S116-1), the first detection information assigning unit 204E assigns the first detection information (first detection information 207B) indicating the medicine and/or equipment, to the image (image for medical use) from which the medicine and/or equipment is detected (step S116-2), and the processing proceeds to step S116-3. In a case where the medicine and/or equipment is not detected (NO in step S116-1), the processing proceeds to step S116-3 without the first detection information assigning unit 204E assigning the first detection information.

In step S116-3, the second detection information assigning unit 204F (second detection information assigning unit) determines whether the second detection unit 204D has detected the region of interest. In a case where the region of interest is detected (YES in step S116-3), the second detection information assigning unit 204F assigns the second detection information (second detection information 207C) indicating the region of interest, to the image (image for medical use) from which the region of interest is detected (step S116-4), and the processing proceeds to step S116-5. In a case where the region of interest is not detected (NO in step S116-3), the processing proceeds to step S116-5 without the second detection information assigning unit 204F assigning the second detection information. In step S116-5, it is determined whether the first detection information assigning unit 204E and the second detection information assigning unit 204F have ended the processing for all of the images, and in a case where the processing is ended (YES in step S116-5), the processing returns to the flowcharts in FIGS. 7 and 8 (step S118 in FIG. 8). In a case where the processing is not ended (NO in step S116-5), the processing returns to step S116-1.

In steps described above, the first detection information assigning unit 204E can assign, as the first detection information, the type and name of the medicine and/or equipment and the contents of the procedure performed using the detected medicine and/or equipment. Further, the second detection information assigning unit 204F can assign, as the second detection information, the type (lesion, lesion candidate, or the like), size, and shape of the region of interest, for example.

<List Display of Image for Medical Use>

In a case where the processing for the first detection information and the second detection information is ended, the display control unit 204B (display control unit) displays the captured images (plurality of images for medical use) in a list on the monitor 400 (step S118: display control step). The setting of the list display can be set through the display condition setting screen shown in FIG. 10, similarly to the setting of the imaging conditions described using FIG. 9. The user performs a display condition setting operation using the operation unit 208, and the display control unit 204B sets the display conditions on the basis of the operation. The setting of the display conditions may be performed before the imaging, during the imaging, or after the imaging. The items and contents shown in FIG. 10 are examples of the display conditions, and other items and contents may be adopted.

<Aspect 1 of Display Form of List>

Figure 12A:
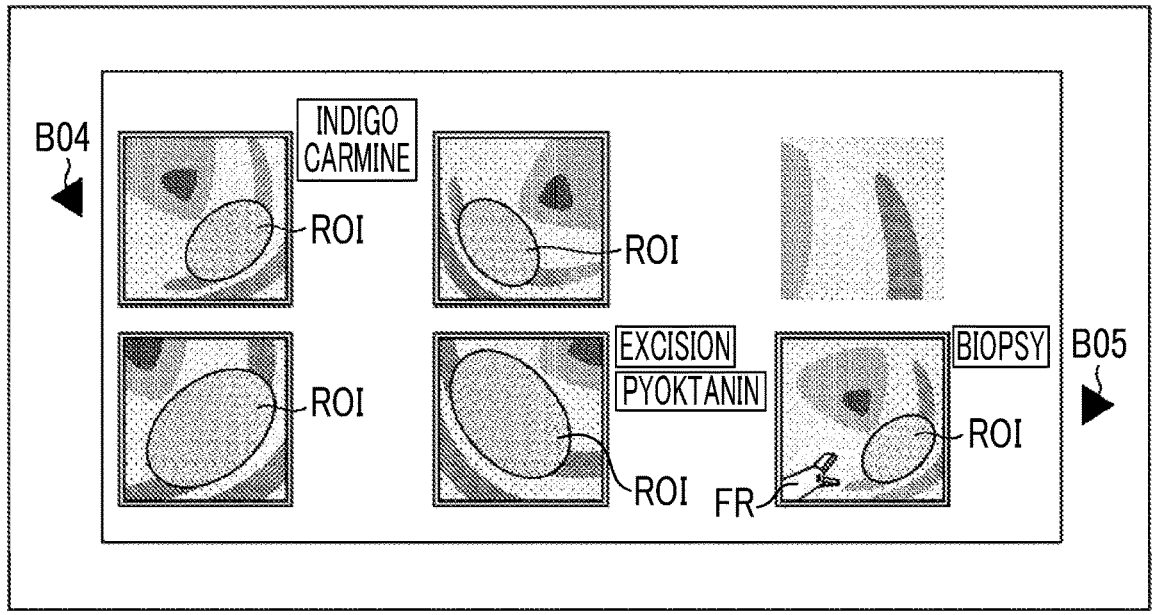
FIGS. 12A and 12B are diagrams showing aspects of a list display of images.
Figure 12B:
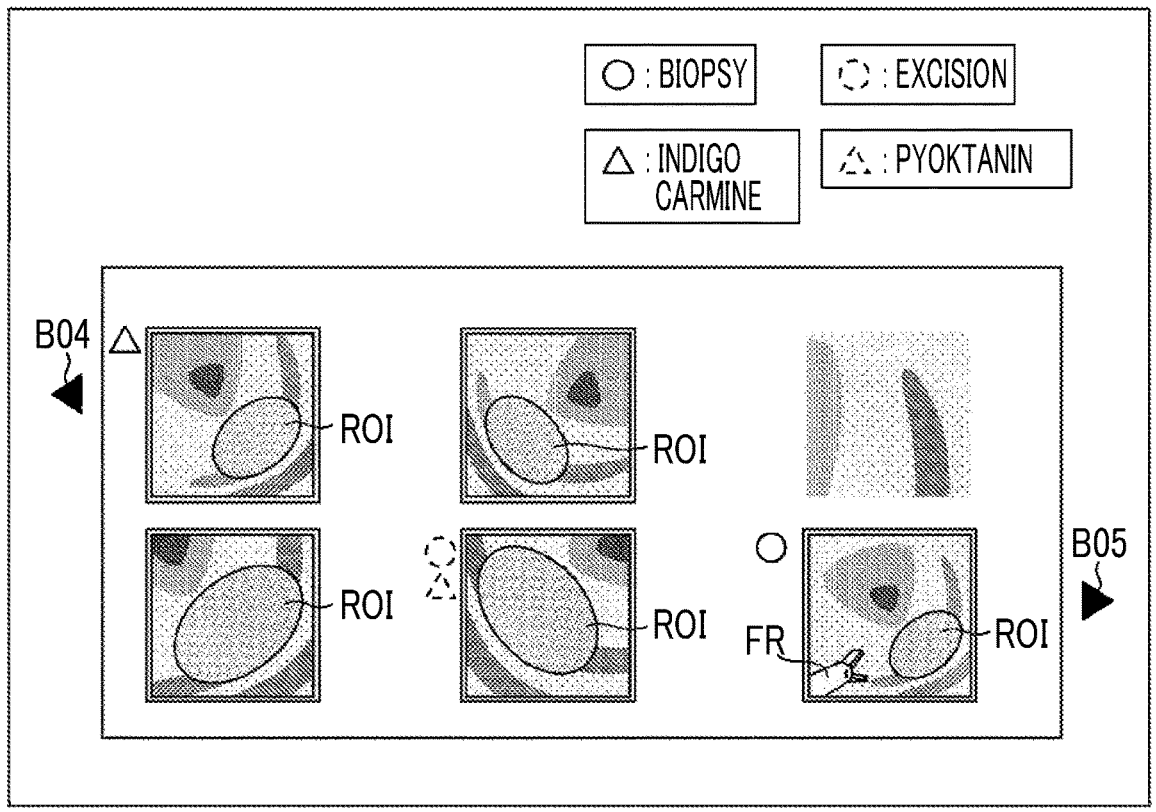

FIGS. 12A and 12B are diagrams showing Aspect 1 of the list display. In Aspect 1, the images are displayed in a list on the monitor 400 (display device) with the first detection information and the second detection information assigned in step S116 being assigned using characters and/or symbols. Specifically, in an example shown in FIG. 12A, the first detection information (name of medicine, contents of procedure) is assigned to the image as character information, and in an example shown in FIG. 12B, the first detection information is assigned to the same image as in FIG. 12A, as symbols. These characters and symbols may be given different numerals or colors depending on the contents. Such image display control is performed by the display control unit 204B.

In FIGS. 12A and 12B, the image with a double-lined frame border (example of second detection information graphically displayed) indicates an image from which the region of interest (region of interest ROI) is detected. In FIGS. 12A and 12B, the upper right image is an image with no frame border because the region of interest is not detected, and the lower right image is an image from which the region of interest ROI and the forceps FR are detected. It is possible to present useful information (the displayed image is an image that is highly necessary to be checked) to a user by displaying the image from which the region of interest is detected in a distinguishable manner, and it is possible for a user to efficiently perform diagnosis, report creation, and the like. A button B04 is a button for causing images which are captured before the displayed images to be displayed, and a button B05 is a button for causing images which are captured after the displayed images to be displayed.

<Aspect 2 of Display Form of List>

Figure 13:
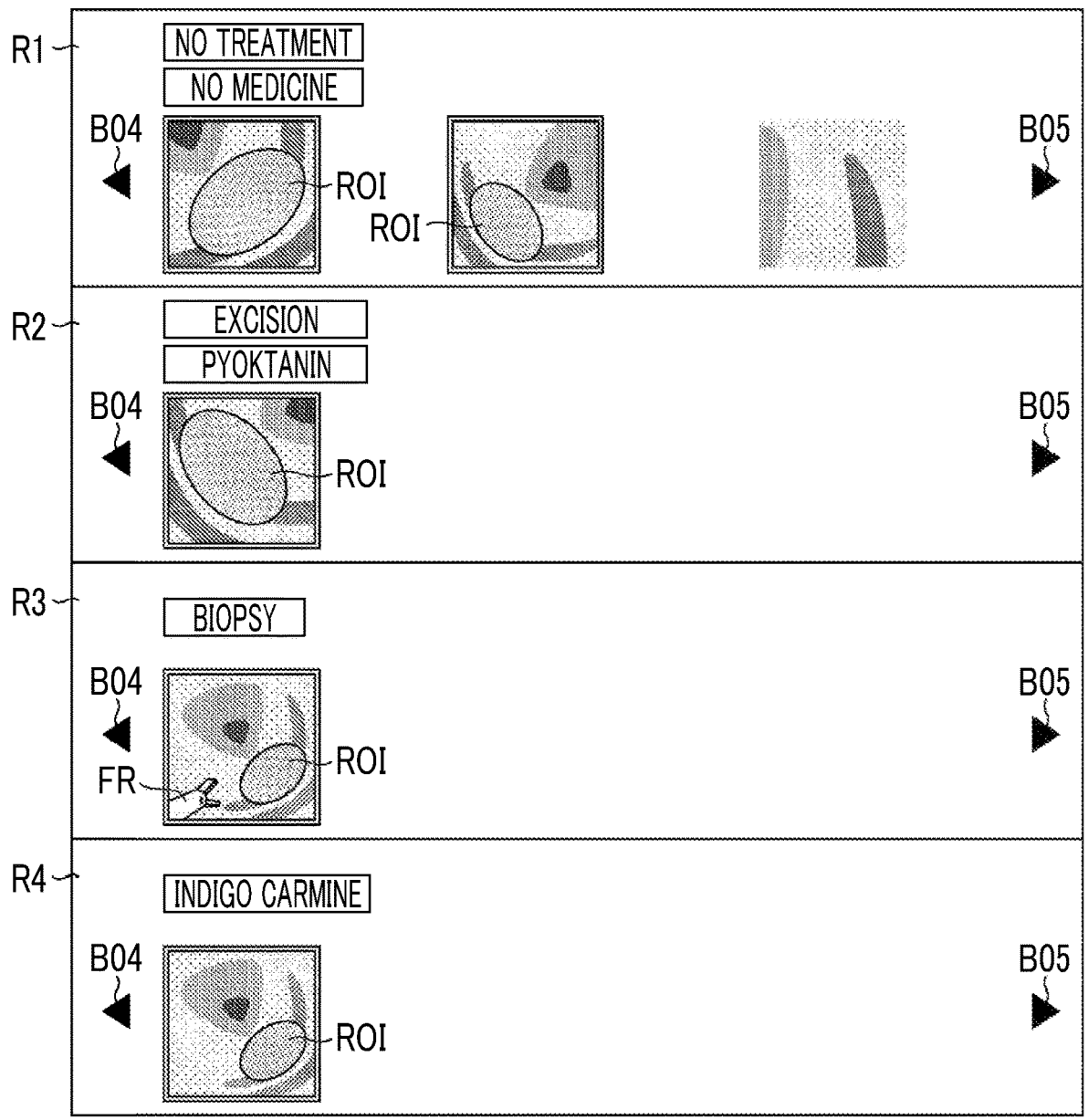
FIG. 13 is another diagram showing an aspect of a list display of images.

In Aspect 2, the display control unit 204B displays the images (plurality of images for medical use) in a list in an arrangement according to the feature of the medicine and/or equipment, on the monitor 400. For example, in case of the same image as in FIGS. 12A and 12B, in Aspect 2, the display positions of the images are divided into regions R1 to R4 according to the type of the medicine and/or equipment as shown in FIG. 13. Further, at the time of the display, the display positions are changed according to the number of images belonging to the same type (the type to which a large number of images belongs is displayed on the upper side).

<Aspect 3 of Display Form of List>

Figure 14A:
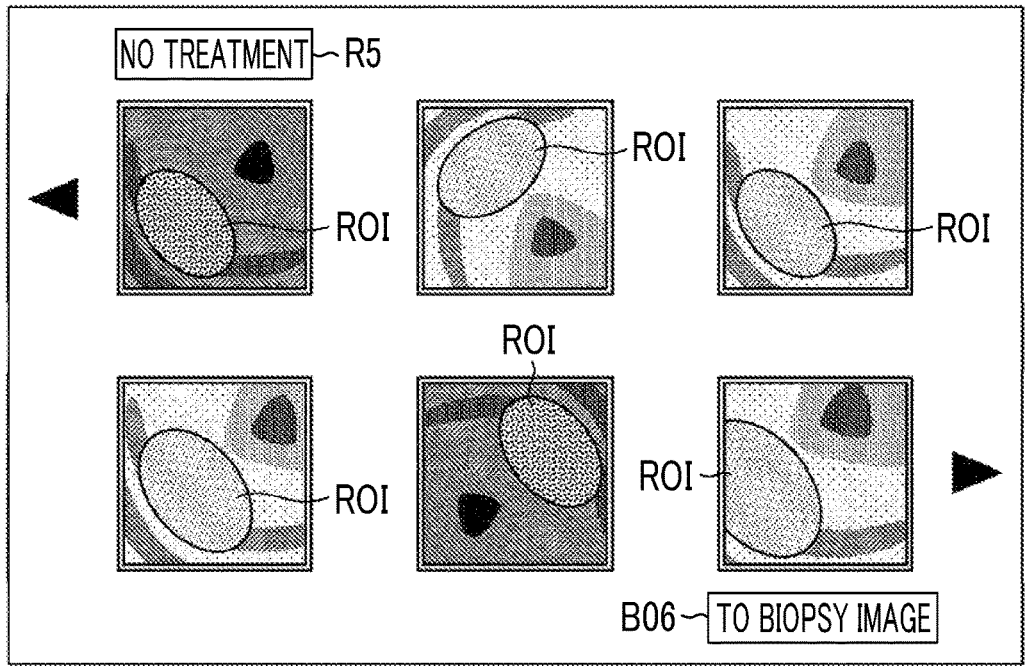
FIGS. 14A and 14B are still other diagrams showing aspects of a list display of images.
Figure 14B:
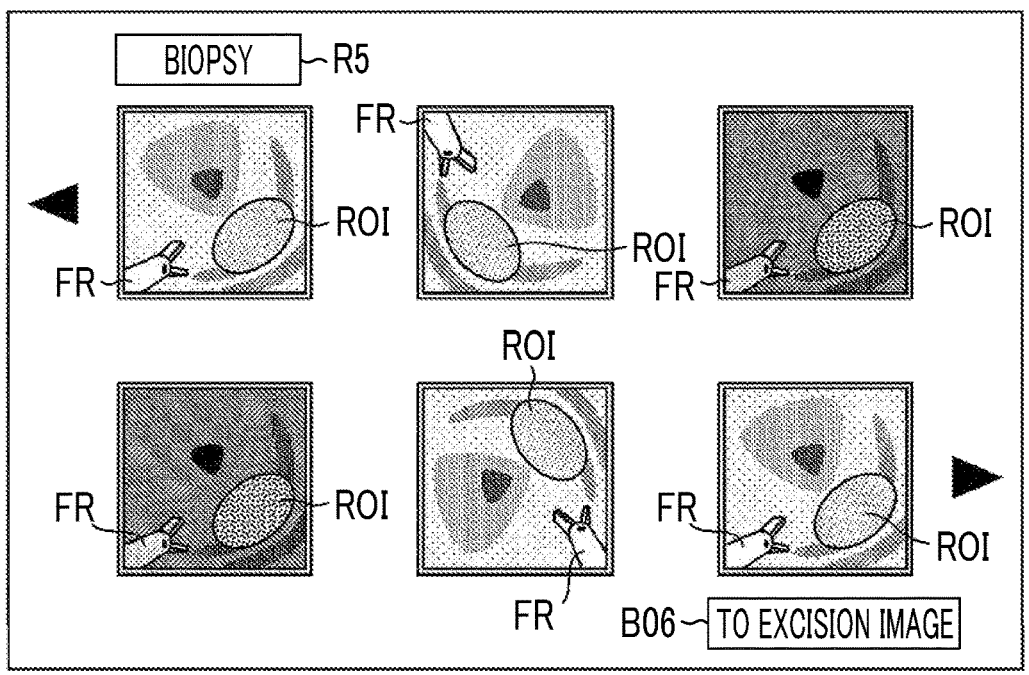

In Aspect 3, the feature (type of the medicine and/or equipment, contents of the procedure, presence or absence of the region of interest, or the like) of the image to be displayed is designated on the basis of the user's operation, and the display control unit 204B displays only the images having the designated feature in a list. Specifically, in a case where the user performs an operation for designating features through the keyboard and/or the mouse of the operation unit 208 or the touch panel of the monitor 400, according to the operation, the feature designation unit 204G (feature designation unit) designates the feature of the image to be displayed, and the display control unit 204B displays the images in a list on the monitor 400 according to the designated feature. FIGS. 14A and 14B are examples of the display according to Aspect 3. FIG. 14A shows an aspect in which only the images with "no treatment" are displayed in a list, and the designated feature ("no treatment") of the image is displayed in a region R5 on the upper left side of the screen. Further, a button B06 for causing the images of another type ("biopsy image") to be displayed is displayed on the lower right side of the screen, and in a case where the user operates the button B06 through the operation unit 208, the "biopsy" is designated as the feature of the image, and only the biopsy images are displayed in a list as shown in FIG. 14B. According to this, the display control unit 204B changes the type of the images displayed in a list, in the region R5 to the "biopsy", and changes the display of the button B06 to another feature ("excision" in this case).

<Aspect 4 of Display Form of List>

Figure 15:
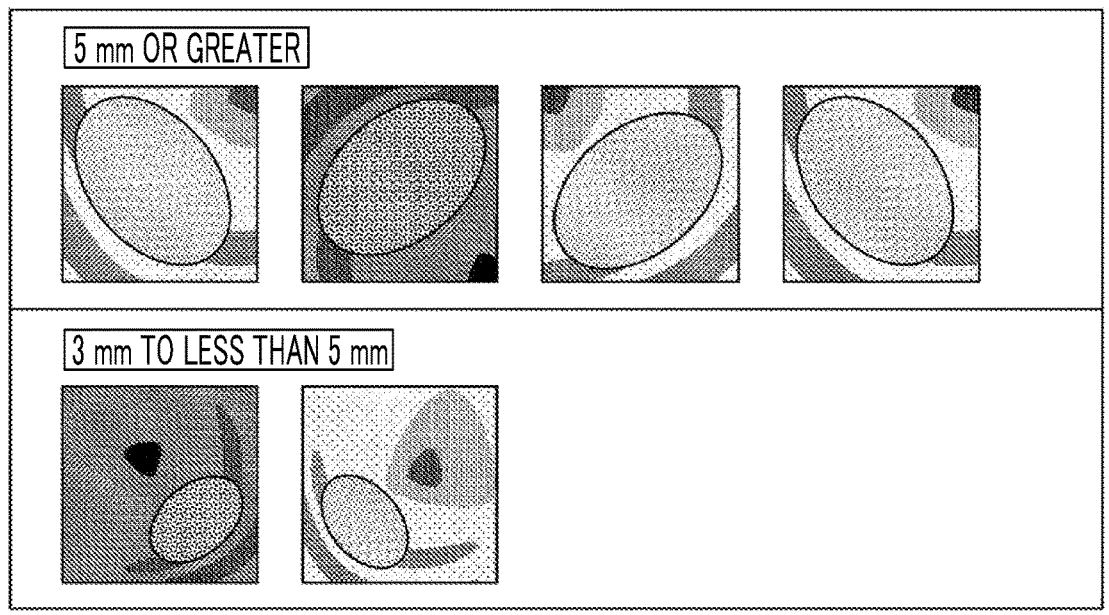
FIG. 15 is still another diagram showing an aspect of a list display of images.
Figure 16:
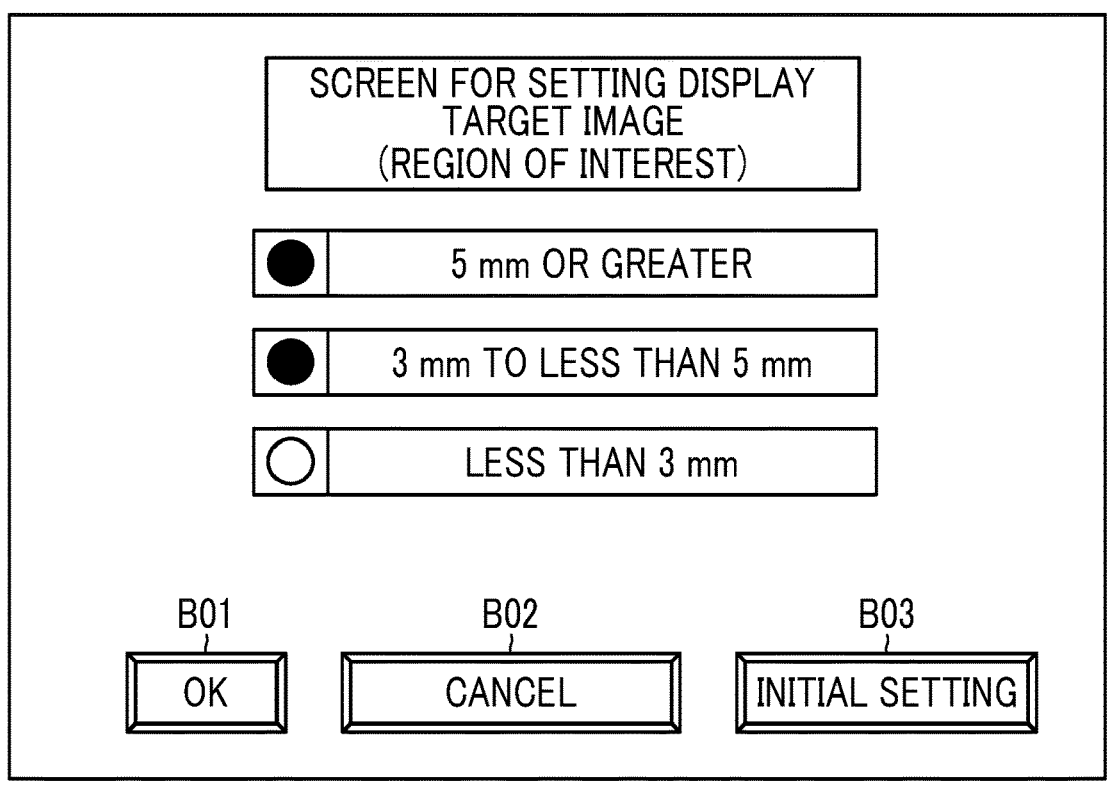
FIG. 16 is another diagram showing an example of the display condition setting screen.

In Aspect 4, the display control unit 204B displays only the images from which the region of interest is detected, in a list. At the time of the display, the display positions are changed according to the feature (for example, size) of the region of interest. Specifically, as shown in the example of FIG. 15, only the images from which the region of interest is detected are displayed in a list according to the size (in the example of FIG. 15, "5 mm or greater" and "3 mm to less than 5 mm") of the region of interest. The setting of the size of the region of interest for the list display can be performed through a screen (image from which a region of interest having a checked type of size is detected is displayed; black circle indicates the checked type) shown in FIG. 16, for example. The size of the region of interest can be calculated on the basis of the imaging conditions (imaging magnification, number of pixels of the region of interest, and the like) by the second detection unit 204D, but instead of or in addition to the calculation of the size by the second detection unit 204D, scales for measuring a size or a marker may be displayed together with the image.

<Preservation of Designated Image>

Figure 17:
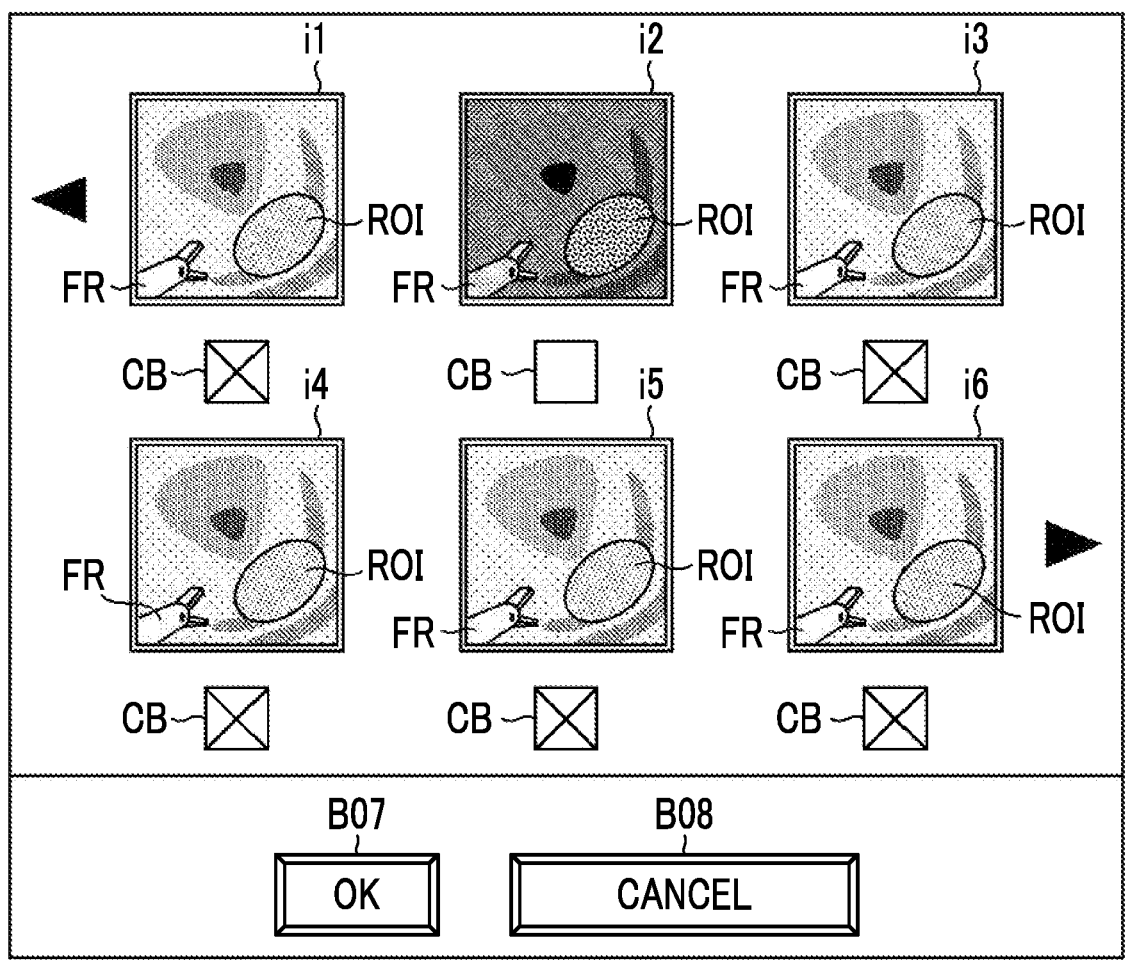
FIG. 17 is a diagram showing an aspect of preservation of a designated image.

In a case where the list display of images in step S118 is ended, the image processing unit 204 (storage control unit 204H) determines whether there is a designated image to be preserved (step S120 in FIG. 8). This determination can be performed in a manner that checkboxes CB are provided to images i1 to i6 displayed in a list as shown in the example of FIG. 17 and the storage control unit 204H determines whether there is a checked image at the time point at which a button B07 is operated. A button B08 is a cancel button. The storage control unit 204H preserves the images of which the checkbox CB is checked (in the example of FIG. 17, the images i1, i3, i4, i5, and i6) in the storage unit 207 as the designated images 207D (step S122). These images can be attached (associated) to a template of a diagnostic report, and thus report creation can be efficiently performed.

The storage control unit 204H stores the first detection information and the second detection information assigned in step S116 as the first detection information 207B and the second detection information 207C to be associated with the designated image 207D in the storage unit 207 (step S122; refer to FIG. 5). In this case, the storage control unit 204H stores information for associating the designated image 207D with the first detection information 207B and the second detection information 207C, as the association information 207E (refer to FIGS. 5 and 6) in the storage unit 207.

In a case where the designated image is preserved, the CPU 210 and the image processing unit 204 determine whether to end the processing (step S124). In case of YES, the processing is ended, and in case of NO, the processing returns to the start of displaying the live view image in step S104.

<Another Aspect of Imaging and Display>

Another aspect of the imaging and display of the image for medical use will be described. An aspect described below can be executed according to the setting through the imaging condition setting screen (FIG. 9) and the display condition setting screen (FIG. 10).

<Automatic Imaging According to Detection of Region of Interest>

In the imaging condition setting screen in FIG. 9, in a case where "detection of a region of interest" (region V01) and "automatic imaging at the time of detection of a region of interest" (region V02) are ON, the detection of the region of interest and the automatic imaging at the time of detection are executed. Specifically, in a case where the second detection unit 204D detects a region of interest from a frame image (frame image of a live view image or a video for recording formed of a plurality of frame images) (YES in step S105-1 in FIG. 18), the image for medical use is acquired by the imaging optical system 130 and the image-for-medical-use acquisition unit 204A (step S108). The display control unit 204B displays the images which are automatically captured according to the detection of the region of interest, in a list as shown in FIG. 15. The detection of the region of interest (lesion candidate or the like) can be performed similarly to the detection described in step S114.

Detection of the medicine and/or equipment and automatic imaging according to the detection can be executed by the condition setting (ON in the regions V03 to V06) through the imaging condition setting screen in FIG. 9, similarly to the case of the above-described region of interest, and the images can be displayed.

According to the aspect in which automatic imaging is performed according to the detection of the region of interest and the medicine and/or equipment, it is possible for a user to easily acquire and display an image suitable for diagnosis, and thus to efficiently perform report creation.

<Static Image Capturing in Parallel with Video Capturing>

In the above-described aspect, a case in which the live view image is acquired and displayed (step S104) and the static image is captured according to the user's instruction (steps S106 and 108) in the flowcharts shown in FIGS. 7 and 8 is described, but the image capturing is not limited to such an aspect. The static image may be captured according to the user's instruction while the video is captured. Specifically, as shown in the flowchart of FIG. 19, after the start of displaying the live view image in step S104, the image-for-medical-use acquisition unit 204A starts the video capturing (step S105-3) according to a video capturing instruction through the operation unit 208 and/or the imaging button BT4 (YES in step S105-2). Further, the image-for-medical-use acquisition unit 204A captures a static image (step S105-5) according to the static image capturing instruction through the operation unit 208 and/or the imaging button BT4 (YES in step S105-4), and the processing of steps S105-4 and S105-5 is repeated until the capturing of the static image and the video is ended (YES in step S105-6). In a case where the capturing of the static image and the video is ended (YES in step S105-6), the processing proceeds to step S112 in FIG. 7. According to such an aspect, it is possible to capture a static image in a particularly notable situation while capturing the video for continuous observation.

As described above, according to the first embodiment, it is possible to present useful information (detection information) to a user, and it is possible for a user to efficiently perform diagnosis, report creation, and the like.

Second Embodiment

Figure 20:
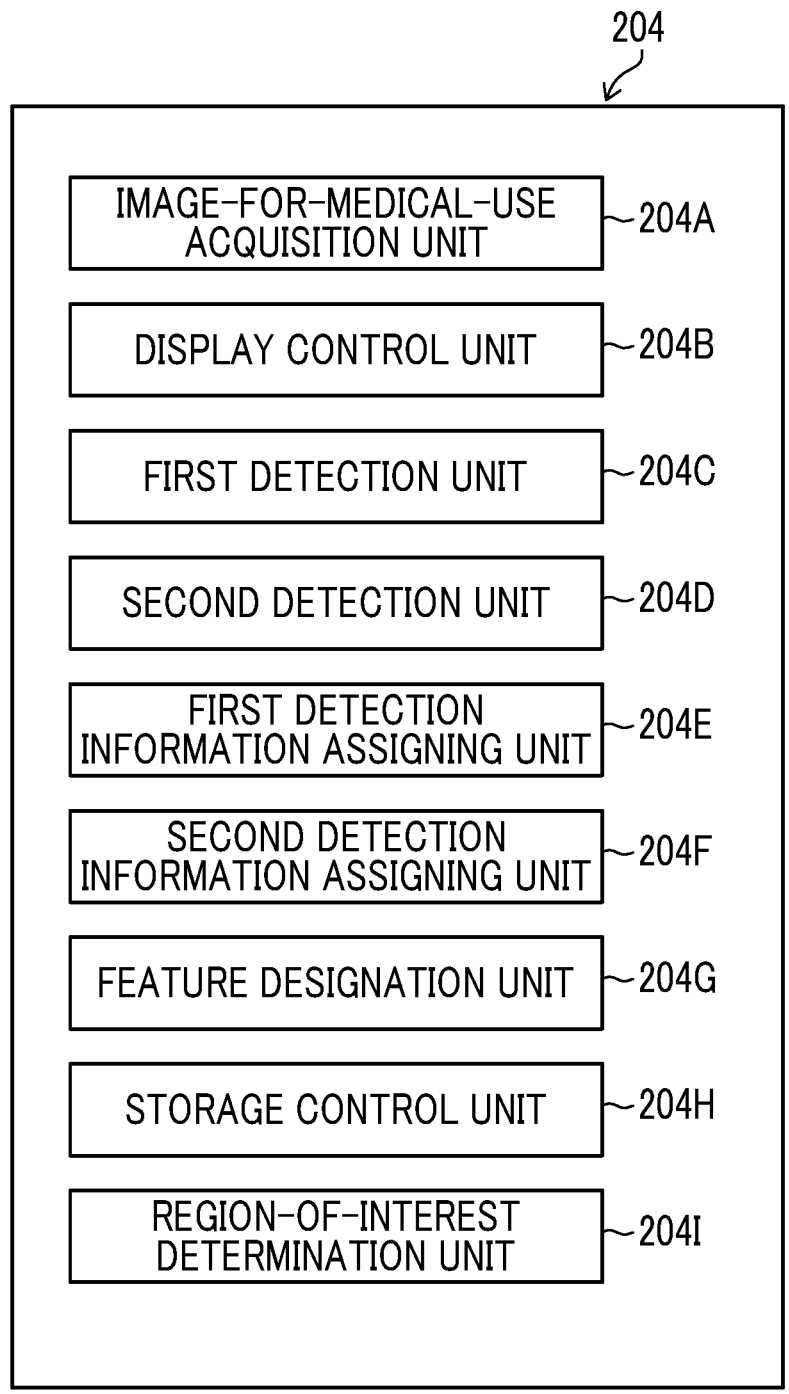
FIG. 20 is a diagram showing a functional configuration of an image processing unit according to a second embodiment.

In the first embodiment, the first detection information and the second detection information are assigned to the image from which the medicine and/or equipment and the region of interest are actually detected (refer to FIG. 11), but in the second embodiment, in a case where a condition is satisfied, the first detection information is assigned to the image from which the medicine and/or equipment is not actually detected. Assigning the detection information in the second embodiment will be described below. The configuration of the endoscope system in the second embodiment is different from the first embodiment in that the image processing unit 204 includes a region-of-interest determination unit 204I (region-of-interest determination unit; refer to FIG. 20). However, since other constituents are the same as those in the first embodiment, the same reference numerals are given to the same constituents and the description thereof is omitted.

<Assigning Detection Information Based on Comparison with Other Images Displayed in List (Aspect 1)>

In a case where the first detection information is assigned only to the image in which the medicine and/or equipment is actually shown, the detection information cannot be assigned to the image in which the medicine and/or equipment is not shown due to the capturing of the image before the treatment or before the application of the medicine with respect to the lesion area (region of interest). However, even in case of such an image in which the medicine and/or equipment is not shown, it is preferable that the fact that "the image is associated with the treatment for the region of interest" can be grasped. In Aspect 1, the determination on "whether the same region of interest as that included in the image from which the medicine and/or equipment is detected is shown" in the plurality of images displayed in a list is performed, and in case of the image in which the same region of interest is shown, even if the medicine and/or equipment is not detected, the first detection information is assigned. The list display of the images is performed on the basis of the first detection information assigned in this manner. According to Aspect 1, even in case of the image in which the medicine and/or equipment is not shown, it is possible for a user to grasp that "the image is associated with the treatment for the region of interest".

Figure 21:
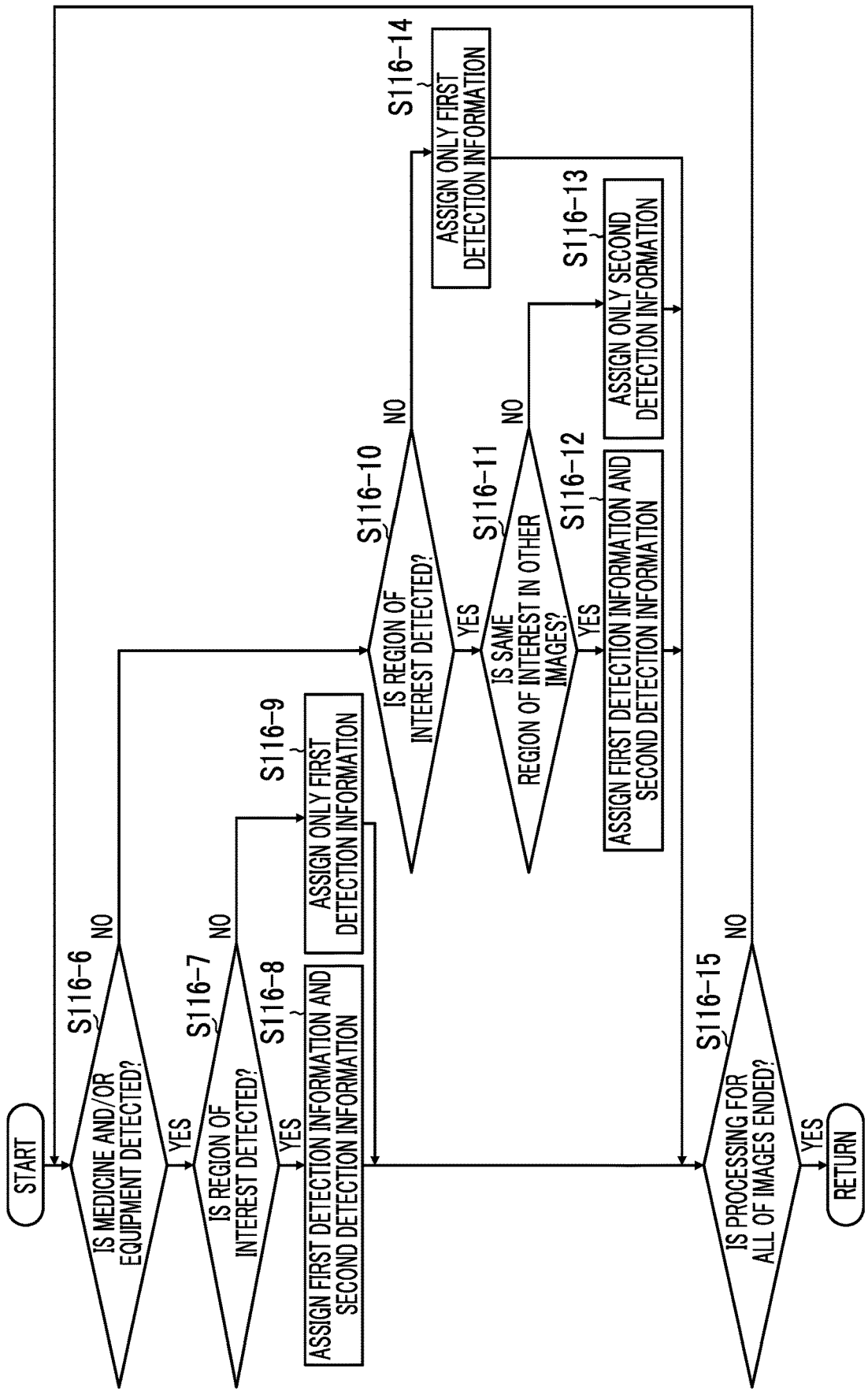
FIG. 21 is a flowchart showing processing of assigning the first detection information and the second detection information.

FIG. 21 is a flowchart showing the details of assigning detection information (corresponding to step S116 of FIG. 7) in the second embodiment (Aspect 1). The first detection information assigning unit 204E determines whether the first detection unit 204C has detected the medicine and/or equipment from a target image (each image constituting a plurality of images for medical use displayed in a list; determination target for assigning detection information) (step S116-6). The determination can be performed on the basis of the results of step S112. In a case where the medicine and/or equipment is detected (YES in step S116-6), the processing proceeds to step S116-7, and the second detection information assigning unit 204F determines whether the second detection unit 204D has detected the region of interest from a target image. The determination can be performed on the basis of the results of step S114. In a case where the region of interest is detected (YES in step S116-7), the first detection information assigning unit 204E assigns the first detection information (first detection information 207B) indicating the medicine and/or equipment, to the target image (step S116-8).

Further, in step S116-8, the second detection information assigning unit 204F assigns the second detection information (second detection information 207C) indicating the region of interest to the target image. In a case where the medicine and/or equipment is detected but the region of interest is not detected from the target image (NO in step S116-7), only the first detection information is assigned by the first detection information assigning unit 204E (step S116-9). In steps described above, the first detection information assigning unit 204E can assign, as the first detection information, the type and name of the medicine and/or equipment and the contents of the procedure performed using the detected medicine and/or equipment. Further, the second detection information assigning unit 204F can assign, as the second detection information, the type (lesion, lesion candidate, or the like), size, and shape of the region of interest, for example.

Meanwhile, even in a case where the medicine and/or equipment is not detected from the target image (NO in step S116-6), the second detection information assigning unit 204F determines whether the second detection unit 204D has detected the region of interest (step S116-10). The determination can be performed on the basis of the results of step S114. In a case where the region of interest is detected (YES in step S116-10), that is, in a case where the medicine and/or equipment is not detected but the region of interest is detected from the target image, the processing proceeds to step S116-11. In step S116-11, it is determined "whether the same region of interest as that included in the target image is included in another image (comparison image), from which the medicine and/or equipment is detected, among the plurality of images for medical use displayed in a list". The determination on the sameness of the region of interest in step S116-11 can be performed by the region-of-interest determination unit 204I on the basis of, for example, the similarity degree of the image, the feature quantity of the image, information of imaging time of each image, the motion vector between images, and combinations of these determination criteria. Whether the medicine and/or equipment is detected from the comparison image can be determined on the basis of the results of step S112.

Figure 22:
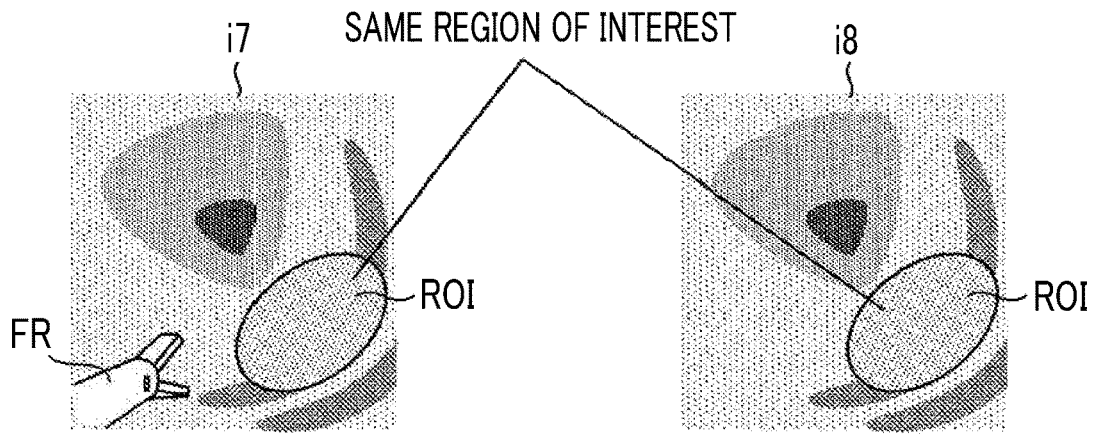
FIG. 22 is a diagram showing an aspect of assigning detection information based on comparison with another image.

In a case where the same region of interest is included in another image (comparison image) (YES in step S116-11), the second detection information assigning unit 204F assigns the second detection information to the target image, and further, the first detection information assigning unit 204E assigns the first detection information to the target image (step S116-12). The first detection information to be assigned to the target image may be exactly the same as the comparison image, or may be changed to be distinguished that the information is assigned in consideration of the sameness of the region of interest. For example, the detection information such as "biopsy equipment: deemed to be detected" can be assigned. The aspect of assigning detection information in steps S116-11 and S116-12 is shown in FIG. 22. In the example shown in FIG. 22, the biopsy equipment is detected from an image i7 (comparison image), and the biopsy equipment is not detected from an image i8 (target image), but the region of interest included in the image i8 is the same as the region of interest included in the image i7, and thus the detection information (first detection information) of "biopsy equipment: detected" is assigned to the image i8. Similarly, even in a case where a medicine is detected from the comparison image, the first detection information assigning unit 204E assigns the first detection information (for example, "crystal violet: detected", "crystal violet: deemed to be detected") to the target image.

In a case where the processing for one image is ended, it is determined whether the first detection information assigning unit 204E and the second detection information assigning unit 204F have ended the processing for all of the images (all of the plurality of images displayed in a list) in step S116-15, and in a case where the processing is ended (YES in step S116-15), the processing returns to the flowchart in FIG. 8 (step S118). In a case where the processing is not ended (NO in step S116-15), the processing returns to step S116-6).

In this manner, in the second embodiment (Aspect 1), the first detection information is assigned to "the image (target image) in which the medicine and/or equipment is not actually shown but the same region of interest as that in the image (comparison image) from which the medicine and/or equipment is detected is included". The list display of the images is performed in an aspect according to the first detection information and the second detection information as described above for the first embodiment. According to the second embodiment (Aspect 1), it is possible to present useful information (even in case of the image in which the medicine and/or equipment is not shown, "the image is associated with the treatment for the region of interest") to a user.

In a case where the same region of interest is not included in another image (NO in step S116-11), only the second detection information indicating the region of interest is assigned to the image by the second detection information assigning unit 204F (step S116-13). Further, in case of NO in step S116-10, that is, in a case where neither the medicine and/or equipment nor the region of interest is detected, neither the first detection information nor the second detection information is assigned (step S116-14).

<Assigning Detection Information Based on Comparison with Frame Image of Video (Aspect 2)>

In Aspect 1 described above, the detection information is assigned on the basis of the results of comparing one image with another image among a plurality of images displayed in a list. However, in Aspect 2, detection information is assigned by comparing each image (target image) included in the plurality of images for medical use displayed in a list with the image (comparison image) which is a plurality of frame images constituting a video and from which the medicine and/or equipment is detected.

In a case where the first detection information and the second detection information are assigned to the captured image, the user may not capture a scene of using the medicine and/or equipment (the image in which the medicine and/or equipment is shown may not be included in a plurality of images displayed in a list). In this case, it is difficult to determine that the target image is an image relating to the medicine and/or equipment, only by comparing the captured images, and the detection information may not be properly assigned in some cases. Therefore, in Aspect 2, detection of medicine and/or equipment is performed for a plurality of frame images constituting a video acquired during the inspection, and it is determined whether the same region of interest is shown between the target image and the frame image (comparison image) from which the medicine and/or equipment is detected. In a case where the same region of interest is shown, detection information is assigned to the target image. By processing in this manner, even in a case where the image in which the medicine and/or equipment is shown is not included in the images displayed in a list, the first detection information indicating the medicine and/or equipment can be assigned.

Figure 23:
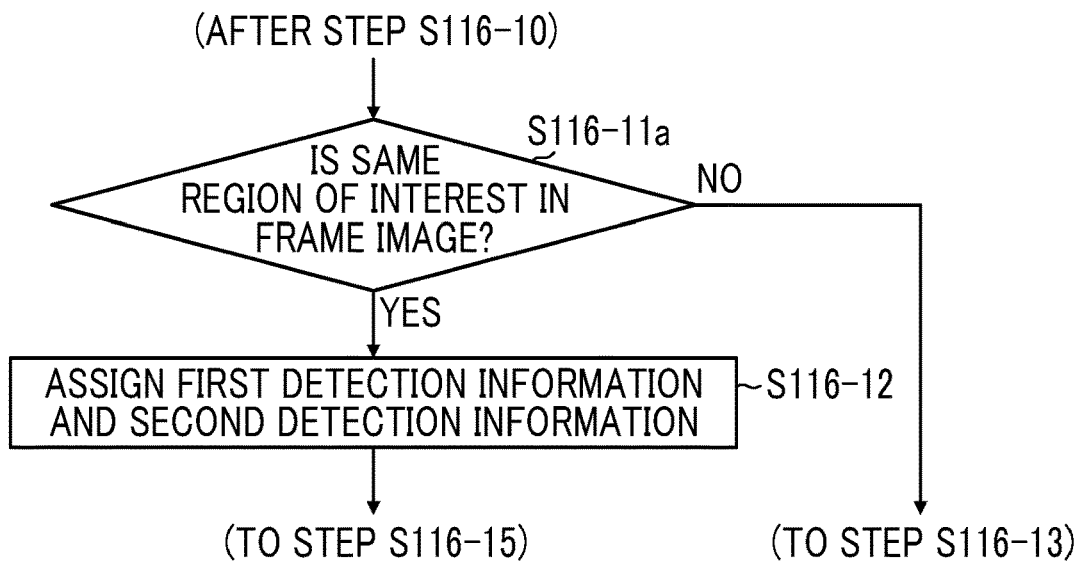
FIG. 23 is a flowchart showing processing of assigning detection information based on comparison with a frame image.

The processing of Aspect 2 is the same as that of Aspect 1. In Aspect 2, instead of "another image" in step S116-11 of FIG. 21, an image which is included in the plurality of frame images constituting the video and from which the medicine and/or equipment is detected becomes the comparison image. The capturing of the static image in parallel with the capturing of the video can be performed according to the above-described aspect described for FIG. 19, for example. The processing for comparison between the target image and the comparison image in Aspect 2 is shown in FIG. 23 (step S116-11a). Whether the medicine and/or equipment and the region of interest are detected can be determined on the basis of the results of steps S112 and S114. In case of YES in step S116-11a, in addition to the second detection information, the first detection information is assigned by the first detection information assigning unit 204E in step S116-12. The first detection information assigned to the target image in step S116-12 may be exactly the same as the comparison image, or may be changed to be distinguished that the information is assigned in consideration of the sameness of the region of interest. For example, the detection information such as "biopsy equipment: deemed to be detected" can be assigned.

In this manner, in the second embodiment (Aspect 2), the first detection information is assigned to "the image (target image) in which the medicine and/or equipment is not actually shown but the same region of interest as that in the image (comparison image) from which the medicine and/or equipment is detected is included". The list display of the images is performed in an aspect according to the first detection information and the second detection information, similarly to Aspect 1. According to Aspect 2, it is possible to present useful information (even in case of the image in which the medicine and/or equipment is not shown, "the image is associated with the treatment for the region of interest") to a user.

As described in Aspects 1 and 2, even in the second embodiment, it is possible to present useful information (detection information) to a user, and it is possible for a user to efficiently perform diagnosis, report creation, and the like. Similarly to the above description for the first embodiment, the detection of the region of interest and the determination on "whether the same region of interest is shown" may be performed using the results of machine learning (deep learning or the like).

(Additional Remarks)

Configurations to be described below are also included in the scope of the invention in addition to the above-described aspects of the embodiments.

(Additional Remark 1)

A medical image processing device comprising: a medical image analysis processing unit that detects a notable region, which is a region to be notable, on the basis of a feature quantity of pixels of a medical image; and a medical image analysis result acquisition unit that acquires an analysis result of the medical image analysis processing unit.

(Additional Remark 2)

The medical image processing device comprising: a medical image analysis processing unit that detects presence or absence of an object to be notable, on the basis of the feature quantity of pixels of a medical image; and a medical image analysis result acquisition unit that acquires an analysis result of the medical image analysis processing unit.

(Additional Remark 3)

The medical image processing device, wherein the medical image analysis result acquisition unit acquires the analysis result of the medical image from a recording device, and the analysis result includes any one or both of the notable region that is the region to be notable included in the medical image and presence or absence of the object to be notable.

(Additional Remark 4)

The medical image processing device, wherein the medical image is a normal light image that is obtained from the application of light in a white-light wavelength range or light in a plurality of wavelength ranges as the light in a white-light wavelength range.

(Additional Remark 5)

The medical image processing device, wherein the medical image is an image that is obtained from the application of light in a specific wavelength range, and the specific wavelength range is a range narrower than the white-light wavelength range.

(Additional Remark 6)

The medical image processing device, wherein the specific wavelength range is a blue-light wavelength range or a green-light wavelength range of a visible-light wavelength range.

(Additional Remark 7)

The medical image processing device, wherein the specific wavelength range includes a wavelength range of 390 nm to 450 nm or 530 nm to 550 nm, and light in the specific wavelength range has a peak wavelength in a wavelength range of 390 nm to 450 nm or 530 nm to 550 nm.

(Additional Remark 8)

The medical image processing device, wherein the specific wavelength range is a red-light wavelength range of a visible-light wavelength range.

(Additional Remark 9)

The medical image processing device, wherein the specific wavelength range includes a wavelength range of 585 nm to 615 nm or 610 nm to 730 nm, and light in the specific wavelength range has a peak wavelength in a wavelength range of 585 nm to 615 nm or 610 nm to 730 nm.

(Additional Remark 10)

The medical image processing device, wherein the specific wavelength range includes a wavelength range where a light absorption coefficient in oxyhemoglobin is different from that in reduced hemoglobin, and light in the specific wavelength range has a peak wavelength in a wavelength range where a light absorption coefficient in oxyhemoglobin is different from that in reduced hemoglobin.

(Additional Remark 11)

The medical image processing device, wherein the specific wavelength range includes a wavelength range of 400±10 nm, 440±10 nm, 470±10 nm, or 600 nm to 750 nm, and light in the specific wavelength range has a peak wavelength in a wavelength range of 400±10 nm, 440±10 nm, 470±10 nm, or 600 nm to 750 nm.

(Additional Remark 12)

The medical image processing device, wherein the medical image is an in-vivo image of the inside of a living body, and the in-vivo image has information of fluorescence emitted by fluorescent materials.

(Additional Remark 13)

The medical image processing device, wherein the fluorescence is obtained from the application of excitation light, which has a peak wavelength in a wavelength range of 390 nm to 470 nm, to the inside of the living body.

(Additional Remark 14)

The medical image processing device, wherein the medical image is an in-vivo image of the inside of a living body, and the specific wavelength range is an infrared wavelength range.

(Additional Remark 15)

The medical image processing device, wherein the specific wavelength range includes a wavelength range of 790 nm to 820 nm or 905 nm to 970 nm, and light in the specific wavelength range has a peak wavelength in a wavelength range of 790 nm to 820 nm or 905 nm to 970 nm.

(Additional Remark 16)

The medical image processing device, wherein a medical image acquisition unit comprises a special light image acquisition unit that acquires a special light image including information about the specific wavelength range on the basis of a normal light image obtained from the application of light in a white-light wavelength range or light in a plurality of wavelength ranges as the light in a white-light wavelength range, and the medical image is the special light image.

(Additional Remark 17)

The medical image processing device, wherein a signal in the specific wavelength range is obtained from an arithmetic operation based on color information about RGB or CMY included in the normal light image.

(Additional Remark 18)

The medical image processing device further comprising: a feature-quantity-image generation unit generating a feature quantity image from an arithmetic operation based on at least one of the normal light image that is obtained from the application of light in a white-light wavelength range or light in a plurality of wavelength ranges as the light in a white-light wavelength range or the special light image that is obtained from the application of light in a specific wavelength range, wherein the medical image is the feature quantity image.

(Additional Remark 19)

An endoscope apparatus comprising: the medical image processing device according to any one of Additional remarks 1 to 18; and an endoscope that acquires an image from the application of at least one of light in a white-light wavelength range or light in the specific wavelength range.

(Additional Remark 20)

A diagnosis support apparatus comprising: the medical image processing device according to any one of Additional remarks 1 to 18.

(Additional Remark 21)

A medical service support apparatus comprising: the medical image processing device according to any one of Additional remarks 1 to 18.

The embodiment and other aspects of the invention have been described above, but the invention is not limited to the above-described aspects and can have various modifications without departing from the scope of the invention.

EXPLANATION OF REFERENCES

10: endoscope system
100: endoscope body
102: hand operation part
104: insertion part
106: universal cable
108: light guide connector
112: soft portion
114: bendable portion
116: hard distal end portion
116A: distal end-side end face
123: illumination unit
123A: illumination lens
123B: illumination lens
126: forceps port
130: imaging optical system
132: imaging lens
134: image pick-up element
136: drive circuit
138: AFE
170: light guide
200: processor
202: image input controller
204: image processing unit
204A: image-for-medical-use acquisition unit
204B: display control unit
204C: first detection unit
204D: second detection unit
204E: first detection information assigning unit
204F: second detection information assigning unit
204G: feature designation unit
204H: storage control unit
204I: region-of-interest determination unit
205: image input interface
206: video output unit
207: storage unit
207A: captured image
207B: first detection information
207C: second detection information
207D: designated image
207E: association information
208: operation unit
209: voice processing unit
209A: speaker
210: CPU
211: ROM
212: RAM
300: light source device
310: light source
310A: visible light source
310B: infrared light source
330: stop
340: condenser lens
350: light source control unit
400: monitor
A01: button
A02: button
A03: button
A04: button
A05: button
A06: button
A07: button
A08: button
A09: button
A10: button
A11: button
A12: button
B01: button
B02: button
B03: button
B04: button
B05: button
B06: button
B07: button
B08: button
BT1: air/water supply button
BT2: suction button
BT3: function button
BT4: imaging button
C01: region
C02: region
C03: region
C04: region
C05: region
C06: region
C07: region
C08: region
C09: region
C10: region
C11: region
C12: region
CB: checkbox
FR: forceps
R1: region
R2: region
R3: region
R4: region
R5: region
ROI: region of interest
S100 to S124: respective steps of diagnosis support method
V01: region
V02: region
V03: region
V04: region
V05: region
V06: region
V07: region
V08: region
V09: region
V10: region
V11: region
V12: region
i1: image
i2: image
i3: image
i4: image
i5: image
i6: image
i7: image
i8: image

What is claimed is:

1. A diagnosis support system comprising:
a processor configured to:
acquire a plurality of medical images;
detect a medicine and/or equipment from the plurality of medical images by image recognition;
detect a region of interest from the plurality of medical images by image recognition;
assign, to the medical image from which the medicine and/or equipment is detected, first detection information indicating the detected medicine and/or equipment;
assign, to the medical image from which the region of interest is detected, second detection information indicating the detected region of interest,
display, on a display device, the plurality of medical images in a list in a display form according to the first detection information and the second detection information,
determine whether a comparison image among the plurality of medical images has a region of interest that is the same as a region of interest included in a target image among the plurality of medical images, the comparison image is a medical image different from the target image and from which the medicine and/or equipment is detected; and
assign the first detection information to the target image in a case where the comparison image has the region of interest that is the same as the region of interest included in the target image even if the medicine and/or equipment is not detected from the target image.

2. The diagnosis support system according to claim 1:
wherein the processor further configured to:
acquire a video constituted of a plurality of frame images;
detect a region of interest from the plurality of frame images by image recognition;
determine whether a comparison image has a region of interest that is the same as a region of interest in a target image among the plurality of medical images, the comparison image is a frame image among the plurality of frame images and from which the medicine and/or equipment is detected; and
assign the first detection information to the target image in a case where the comparison image has the region of interest that is the same as the region of interest included in the target image even if the medicine and/or equipment is not detected from the target image.

3. The diagnosis support system according to claim 1, wherein the processor configured to acquire an medical image constituting the plurality of medical images according to an imaging instruction operation by a user.

4. The diagnosis support system according to claim 1, wherein the processor configured to acquire an medical image constituting the plurality of medical images according to an imaging instruction operation by a user.

5. The diagnosis support system according to claim 1, wherein the processor configured to display only the medical images from which the region of interest is detected, in a list.

6. The diagnosis support system according claim 1, wherein the processor configured to display the plurality of medical images in the list by adding at least one of characters, numerals, symbols, or colors to the medical image from which the medicine and/or equipment is detected, according to the first detection information, and adding at least one of characters, numerals, symbols, or colors to the medical image from which the region of interest is detected, according to the second detection information.

7. The diagnosis support system according to claim 1, wherein the processor configured to display the plurality of medical images in the list in an arrangement according to a feature of the medicine and/or equipment.

8. The diagnosis support system according to claim 1, wherein the processor configured to display the plurality of medical images in the list in an arrangement according to a feature of the region of interest.

9. The diagnosis support system according to claim 1, wherein the processor further configured to:
designate a feature of the medicine and/or equipment; and
display only the medical image from which the medicine and/or equipment having the designated feature is detected, in the list.

10. An endoscope system comprising:
the diagnosis support system according to claim 1;
the display device; and
an endoscope including
an insertion part that is to be inserted into an object to be examined, and includes a hard distal end portion, a bendable portion connected to a proximal end side of the hard distal end portion, and a soft portion connected to a proximal end side of the bendable portion,
an operation part connected to a proximal end side of the insertion part, and
an image pick-up unit including an imaging lens that forms an optical image of a subject, and an image pick-up element on which the optical image is formed, the imaging lens being provided on the hard distal end portion,
wherein the image sensor acquires the plurality of the medical images by the image pick-up unit.

11. An endoscope system comprising:
the diagnosis support system according to claim 1;
the display device; and
an endoscope including
an insertion part that is to be inserted into an object to be examined, and includes a hard distal end portion, a bendable portion connected to a proximal end side of the hard distal end portion, and a soft portion connected to a proximal end side of the bendable portion,
an operation part connected to a proximal end side of the insertion part, and
an image pick-up unit including an imaging lens that forms an optical image of a subject, and an image pick-up element on which the optical image is formed, the imaging lens being provided on the hard distal end portion,
wherein the image sensor acquires the plurality of the medical images by the image pick-up unit.

12. A diagnosis support method comprising:
acquiring a plurality of medical images;
detecting a medicine and/or equipment used in a case where the plurality of medical images are captured, from the plurality of medical images by image recognition;
detecting a region of interest from the plurality of medical images by image recognition;
assigning, to the medical image from which the medicine and/or equipment is detected, first detection information indicating the detected medicine and/or equipment;

assigning, to the image for medical use from which the region of interest is detected, second detection information indicating the detected region of interest, displaying the plurality of images for medical use in a list in a display form according to the first detection information and the second detection information, determining whether a comparison image among the plurality of medical images has a region of interest that is the same as a region of interest included in a target image among the plurality of medical images, the comparison image is a medical image different from the target image and from which the medicine and/or equipment is detected; and assigning the first detection information to the target image in a case where the comparison image has the region of interest that is the same as the region of interest included in the target image even if the medicine and/or equipment is not detected from the target image.

* * * * *